(12) United States Patent
Levison et al.

(10) Patent No.: US 7,993,855 B2
(45) Date of Patent: Aug. 9, 2011

(54) USE OF ADDITIVES TO LOWER THE RATE OF A BINDING REACTION

(75) Inventors: Stuart Levison, Edgewater, NJ (US); Paul Nix, Jackson, NJ (US); Derek Levison, Edgewater, NJ (US)

(73) Assignee: Aokin AG, Berlin (DE)

( * ) Notice: Subject to any disclaimer, the term of this patent is extended or adjusted under 35 U.S.C. 154(b) by 384 days.

(21) Appl. No.: 12/294,299

(22) PCT Filed: Mar. 16, 2007

(86) PCT No.: PCT/US2007/006681
§ 371 (c)(1),
(2), (4) Date: Jan. 13, 2009

(87) PCT Pub. No.: WO2007/111851
PCT Pub. Date: Oct. 4, 2007

(65) Prior Publication Data
US 2009/0317922 A1  Dec. 24, 2009

Related U.S. Application Data

(60) Provisional application No. 60/785,636, filed on Mar. 24, 2006.

(51) Int. Cl.
*G01N 1/00* (2006.01)
*G01N 33/53* (2006.01)

(52) U.S. Cl. ............ 435/7.21; 435/2; 435/7.1; 436/501; 436/518; 436/522; 422/50

(58) Field of Classification Search .................. None
See application file for complete search history.

(56) References Cited

U.S. PATENT DOCUMENTS
5,371,021 A  12/1994  Oh et al.
5,593,896 A   1/1997  Adamczyk et al.

FOREIGN PATENT DOCUMENTS
EP  0392332 A2  10/1990
WO  8900694     1/1989

OTHER PUBLICATIONS

Gomez-Hens et al.; Stopped-flow Fluorescence Polarization Immunoassay; Bentham Science Publishers, Hilversum, NL, vol. 6, No. 3, May 2003, pp. 177-182.
Levison et al.; Fluorescence Polarization and Intensity Kinetic Studies of Antifluorescein Antibody Obtained at Different Stages of the Immune Response; Biochemistry; vol. 14, No. 17, 1975, pp. 3778-3786.
Perez-Benditino et al; Direct Stopped-Flow fluorescence Polarization Immunoassay of Abused Drugs and Their Metatolites in Urine; Clinical Chemistry, Aug. 1994, vol. 40, No. 8 pp. 1489-1493.
Eremin et al.; Kinetic Determination of 2,4-Dichlorophenoxyacetic Acid by Stopped-Flow Fluorescence Polarization Immunoassay; International Journal of Environmental Analytical Chemistry; vol. 71(2), 1998, pp. 137-146.
Cartwright, Chemiluminescent Delay: An Experiment in Stopped-Flow Kinetics; The Chemical Educator, Feb. 1997, vol. 1, No. 6, pp. 1-12.

*Primary Examiner* — Lisa Cook
(74) *Attorney, Agent, or Firm* — Hoffmann & Baron, LLP

(57) ABSTRACT

A method of lowering the rate of a specific binding reaction in an assay for the detection and/or measurement of an analyte of interest is provided herein. In particular, the method includes providing a fluorescent conjugate of the analyte; a component capable of specifically binding to the analyte and its fluorescent conjugate; and a sample, which includes or is suspected to include the analyte. The method also includes allowing the specific binding component to interact simultaneously or at different times with the fluorescent conjugate of the analyte and the analyte in the sample, thereby forming a detectable complex due to the reaction between the fluorescent conjugate of the analyte and its specific binding component, wherein the reaction is performed in the presence of non-physiological amounts of at least one additive. The method further includes monitoring for the rate of change of the concentration of the detectable complex as a function of the amount of analyte in the sample.

35 Claims, 16 Drawing Sheets

Competitive Inhibition by T4 of anti-T4/F-T4 System

Additive Effects on Specific and Non-specific Binding

PFID vs. Time assay of a rhodamine-labeled T4/anti-T4 system in the presence of an additive.

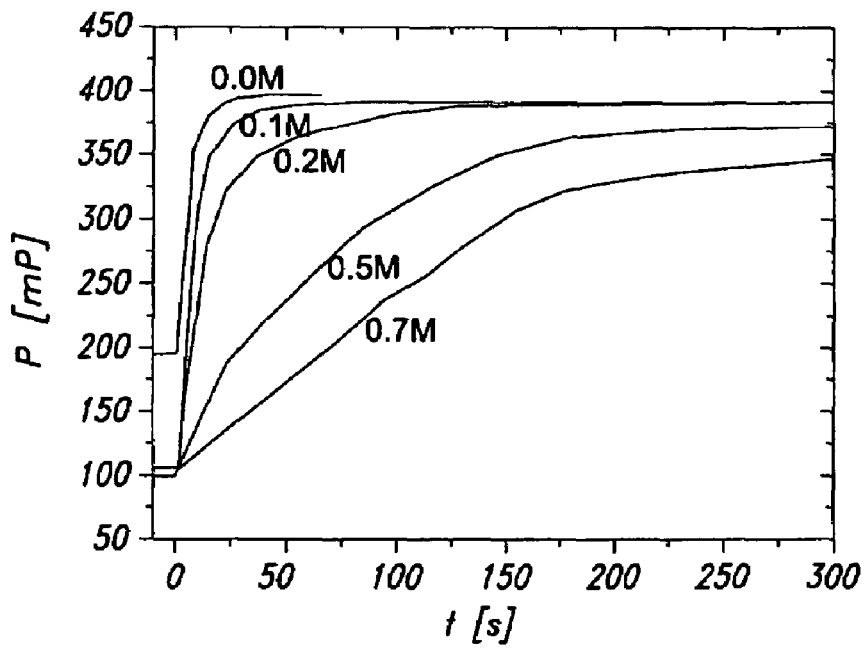

| Reaction No. | Description | dP/dt at t-5s | mP at t-0s |
|---|---|---|---|
| 6-1 | without serum with 0 M additives | 25 | 100 |
| 6-2 | with serum with 0 M additives | 9.7 | 195 |
| 6-3 | with serum with 0.1 M Benzodate | 13.5 | 106 |
| 6-4 | with serum with 0.2 M Benzodate | 13.5 | 100 |
| 6-5 | with serum with 0.5 M Benzodate | 10.1 | 100 |
| 6-6 | with serum with 0.7 M Benzodate | 6.8 | 100 |
| 6-7 | with serum with 1.0 M Benzodate | 3.2 | 100 |

The influence of sodium benzoate additive combined with 10% 2-propanol on the reaction velocity and on the initial non-specific binding of serum components.

FIG. 4

Effects on a fluoresecein-T4/anti-T4 reaction performed in a PBS buffer containing an 5% 2-propanol and differing amounts of the additive sodium benzoate in the absence of unspecific binding substances Effects on a fluorescein-T4/anti-T4 system using differing concentrations of additive sodium benzoate combined with 5% 2-propanol in the presence of theunspecific binding substance BSA.

Effects on a fluorescein-T4/anti-T4 system using differing concentrations of additive guanidine hydrochloride combined with 5% 2-propanol.

Effects on a fluorescein-T4/anti-T4 system using differing concentrations of additive sodium dichloroacetate combined with 5% 2-propanol.

Effects on a fluorescein-T4/anti-T4 system using differing concentrations of additive potassium benzoate combined with 4.75% 2-propanol.

Effects on a fluorescein-T4/anti-T4 system using differing concentrations of additive sodium chloroacetate combined with 4.75% 2-propanol.

Effects on a fluorescein-T4/anti-T4 system using differing concentrations of additive sodium dichloroacetate combined with 4.75% 2-propanol.

Effects on a fluorescein-T4/anti-T4 system using differing concentrations of additive sodium salicylate combined with 4.75% 2-propanol.

Effects on a fluorescein-T4/anti-T4 system using differing concentration of additive N-hydroxsuccinimide combined with 4.75% 2-propanol.

Effects on a fluorescein-T4/anti-T4 system using differing concentration of additive sodium chloride combined with 4.75% 2-propanol.

Effects on a rhodamine-T4/anti-T4 system using differing concentrations of additive sodium benzoate combined with 10% 2-propanol.

Standard Calibration Curve of a rhodamine-T4/anti-T4 in the presence of an additive sodium benzoate combined with 10% 2-propanol.

USE OF ADDITIVES TO LOWER THE RATE OF A BINDING REACTION

FIELD OF THE INVENTION

The present invention relates to methods of lowering the rate of a specific binding reaction between macromolecules and molecules of interest. In particular, the invention relates to the use of additives to lower the rate of reactions in a competitive assay for the detection and/or measurement of an analyte in a sample.

BACKGROUND OF THE INVENTION

Fluorescence polarization and fluorescence intensity measurements provide a powerful means by which macromolecular association reactions can be studied. These fluorescent techniques have been applied to study antigen-antibody, peptide-antibody, hapten-antihapten, protein-ligand, and protein-DNA interactions.

The inherent sensitivity of fluorescence measurements can be used in monitoring the extent of reaction as a fluorescent reactant, F, combines with its macromolecular partner, R:

$$F + R \underset{k_{-1}}{\overset{k_1}{\rightleftharpoons}} F-R \qquad \text{Eq. (1)}$$

where $k_1$ is the forward reaction and $k_{-1}$ is the back reaction such that $(k_1)/(k_{-1}) = K_{(eq)}$.

The investigator can choose to follow changes in the fluorescence polarization (P) and/or the fluorescence intensity (FI). If the reactants do not have natural fluorescence, as in the case of many hapten- or antigen-antibody systems, one of the reactants can be covalently labeled with a fluorescent tag. An increase in the fluorescence polarization of F usually occurs during combination with R, even if there are no concomitant changes in the fluorescence intensity. This is because the polarization increase reflects a slowing down of the rotary brownian motion of the smaller ligand, F, when it becomes attached to the larger species, R. R is in many instances an antibody or a fragment of an antibody, such as an $F_{ab}$ or $F_{ab2}$ (dimer). Equilibrium fluorescence polarization and intensity measurements can be determined in a direct readout polarometer capable of measuring both the degree of fluorescence polarization and the fluorescence intensity of a solution.

Immunoassays have been used in an effort to improve upon the success in detecting analyte substances at very low levels. For example, the use of such techniques has been prompted by the extraordinary successes that have been achieved in the measurement of biological substances by specific immunological reagents and techniques. Available evidence indicates that specific binding antibodies can be obtained even against low molecular weight organic compounds, such as pesticides or other haptens.

Any means of applying an immunochemical reaction to a detection problem ultimately relies upon a binding reaction occurring between a substance (antigen or hapten) and its specific antibody. One means by which this interaction can be employed in measurement and detection has come to be known as "competitive binding assay". In principle, this method requires two reagents. These are a labeled form of the substance to be detected or measured, and an antibody or receptor specifically directed against the substance. The principle of the assay involves a preliminary measurement of the binding of the labeled hapten or antigen (substance being detected) with its antibody and then, a determination of the extent of the inhibition of this binding by known quantities of the unlabeled hapten or antigen, which corresponds to the unknown. From these data, a standard curve can be constructed which shows the degree of binding by the labeled hapten or antigen under certain specified conditions as a function of concentration of the unlabeled hapten or antigen or unknown added.

One way of implementing an immunoassay is to employ a fluorescent label. Usually, fluorescent labeling of one of the reagents e.g. the hapten is important in the carrying out of the immunoassay by means of fluorescence polarization and/or fluorescence intensity measurements. Unlike other immunoassays, such as ELISA, no physical separation of bound from free forms of the labeled hapten is necessary. Therefore a simple rapid optical measurement yields the essential information without physical separation of bound and free labeled materials.

Direct readout polarometers (having a machine time-constant of 0.1 seconds to several minutes) can be used to study slow kinetic reactions (reaction time-constant 10 seconds or longer) as well as reactions near or at equilibrium. These direct readout polarometers (defined as "static" polarometers) are capable of measuring both the degree of fluorescence polarization, $P = (V-H)/(V+H)$ and the fluorescence intensity $(V+H)$. $V-H$ can also be measured and utilized as a parameter. Some antigen-antibody reactions can be slow enough such that they can be studied with the static polarometer. Other antigen-antibody reactions as well as many hapten-antibody reactions occur too rapidly (reaction milliseconds to seconds) to be monitored by the static fluorescence polarization or fluorescence intensity device. Fast reaction technology (e.g. stopped-flow methodology) has been combined with fluorescence polarization and fluorescence intensity techniques to study rapid hapten-antibody, rapid antigen-antibody, rapid enzyme-substrate, rapid substrate-receptor reactions. Such rate assays should lead in principle to simplified and improved assays even when applied to the analysis of real analytes. Yet currently there are few fluorescence polarization or fluorescence intensity rate immunoassays as well as other rate assays involving substrates and receptors. This is because fluorescence polarization and fluorescence intensity stopped-flow devices are expensive, somewhat complicated, and at times limited by background problems. "Static" fluorescence polarometers rate immunoassays require large dilutions of fluorescent reactants and analytes to slow down these fast reactions so that a reasonable time frame (seconds to minutes) can be attained. Others methods used to slow down the reaction are pH and/or temperature changes. These necessary reactant and analyte assay changes (pH, temperature, dilution) lead to background problems and loss of sensitivity. These background problems are severe because the background signal becomes large relative to the specific immunoassay (or assay) signal. The background signal is related to noise originating from photomultiplier noise, solution matrix light scattering and a variety of fluorescent signals coming from irrelevant non-specific binding substances. Therefore, it would be particularly advantageous to provide a competitive-type fluorescence polarization and/or fluorescence intensity immunoassay in which the rate of association reactions of the labeled substance with its specific antibody is substantially reduced. This would allow the investigator to successfully analyze real samples by fluorescence polarization or fluorescence intensity assays without the need for special instrumentation or expensive fast reaction methodology, such as stopped-flow techniques.

As for any homogeneous immunoassay, a limitation of fluorescence polarization and/or fluorescence intensity assays, when applied to analysis of real samples, has been the background signal, which is caused partly by scattered light and partly by the fluorescence of the sample matrix. Scattered light can be caused by macromolecules, such as proteins, and also by a fluorescent label that has a small Stokes shift. One approach to avoid or minimize the background signal has been to measure the rate of the immunochemical reaction between the fluorescent reactant (antigen or hapten) and its specific antibody as the analytical parameter, instead of the signal obtained when the reaction reaches or is close to the equilibrium. Although it is desirable to measure the rate of the reaction to obtain more accurate measurements, the rate of a competitive antigen-antibody or hapten-antibody reaction is usually very fast. Therefore, it has been necessary to obtain data using fluorescence polarization and or fluorescent intensity methods in combination with stopped-flow methods.

Therefore, there is a need to provide improved assays for detecting the presence and/or amount of an analyte in a sample. In particular, it would be advantageous to provide a competitive-type fluorescence polarization and/or fluorescence intensity immunoassay in which the rate of the association reaction of a labeled substance (antigen or hapten) with its specific antibody is substantially reduced. This would allow the investigator to successfully analyze real samples without the need for special instrumentation, such as the stopped-flow fluorescence polarometer, as well as increasing the performance of the stopped-flow devices themselves.

SUMMARY OF THE INVENTION

The present invention is directed to methods for lowering the rate of a competitive reaction between a substance and its specific binding partner by use of a non-physiological amount of at least one additive. This results in an improved assay for the detection and/or measurement of an analyte because no special instrumentation will be required, background signals are minimized, the rate immunoassay is simplified, and/or in addition, special instrumentation performance can be improved.

Before the present invention, it was necessary to combine fluorescence polarization and/or fluorescence intensity methods with stopped-flow methods in order to study fast reactions (e.g., k values are about $10^6$ $M^{-1}$ $sec^{-1}$ or greater), such as hapten-antihapten reactions. Moreover, before the present invention, measurements of initial rates or of differential rates of competitive hapten- or antigen-antibody reactions required the use of both fluorescence polarization and/or fluorescence intensity and stopped-flow methods because these rates are usually quite fast. The present invention is directed to overcoming the need for stopped-flow polarometers to measure fast reactions by using non-physiological amounts of at least one additive in the reaction mixture. The method will also allow improvements made with stopped-flow devices by lowering the rate of reaction. With lower reaction rate processes, higher sensitivity and improved specificity can be achieved with simplicity.

In particular, the present invention provides methods of lowering the rate of a reaction in an assay for the detection and/or measurement of an analyte in a sample. One method includes:

(a) providing a reaction mixture including at least two components selected from (i) a fluorescent conjugate of the analyte; (ii) a component capable of specifically binding to the analyte and its fluorescent conjugate; and (iii) a sample, which includes or is suspected to include the analyte;

(b) providing the component not selected in step (a):

(c) allowing the selected components in the reaction mixture to interact;

(d) adding non-physiological amounts of at least one additive to the reaction mixture or the component of step (b) or both;

(e) combining the reaction mixture and the step (b) component; and (f) monitoring for the rate of change of the concentration of a complex formed due to the combination of the components in step (a) and (b) to determine the concentration of the analyte in the sample.

The present invention also provides a method of lowering the rate of a reaction in an assay for the detection and/or measurement of an analyte in a sample that includes:

(a) providing (i) a fluorescent conjugate of the analyte; (ii) a component capable of specifically binding to the analyte and its fluorescent conjugate; and (iii) a sample, which includes or is suspected to include the analyte;

(b) allowing component (ii) to interact with the fluorescent conjugate of the analyte and the analyte in the sample, thereby forming a detectable complex due to the reaction between the fluorescent conjugate of the analyte and component (ii), wherein the reaction is performed in the presence of non-physiological amounts of at least one additive; and (c) monitoring for the rate of change of the concentration of the complex formed in (b) to determine the concentration of the analyte in the sample.

In some embodiments, the method may include providing a reaction mixture, which includes a fluorescent conjugate of the analyte; and a component capable of specifically binding to the analyte and its fluorescent conjugate. The method may further include providing a sample, which includes or is suspected to include the analyte; and allowing the fluorescent conjugate to react with the specific binding component in a specific binding reaction in the presence and absence of the sample. In some embodiments, the method also includes adding non-physiological amounts of at least one additive to the reaction mixture before binding to lower the rate of the specific binding reaction; and monitoring for the inhibition of the binding of the fluorescent conjugate to its specific binding component as a function of the amount of analyte in the sample.

The fluorescent conjugate (tracer) competes with the analyte in the sample for the antibody. The fluorescent conjugate will only exhibit polarized fluorescence when bound to the antibody, and this will be inversely proportional to the concentration of the analyte in the sample.

In the presence of the unlabeled analyte, a smaller percentage of the labeled analyte is bound to the specific binding component. A standard curve can be constructed from this type of data, which would show fluorescence measurements for certain standard chosen experimental conditions plotted as a function of the amount of unlabeled analyte. An unknown amount of analyte in the sample can then be determined by extrapolation from this standard curve.

BRIEF DESCRIPTION OF DRAWINGS

FIG. 4 is a graph and table of the influence of sodium benzoate combined with a solvent on the reaction rate of a labeled thyroxine with anti-thyroxine and on the non-specific binding.

DETAILED DESCRIPTION OF THE INVENTION

Figure 1:
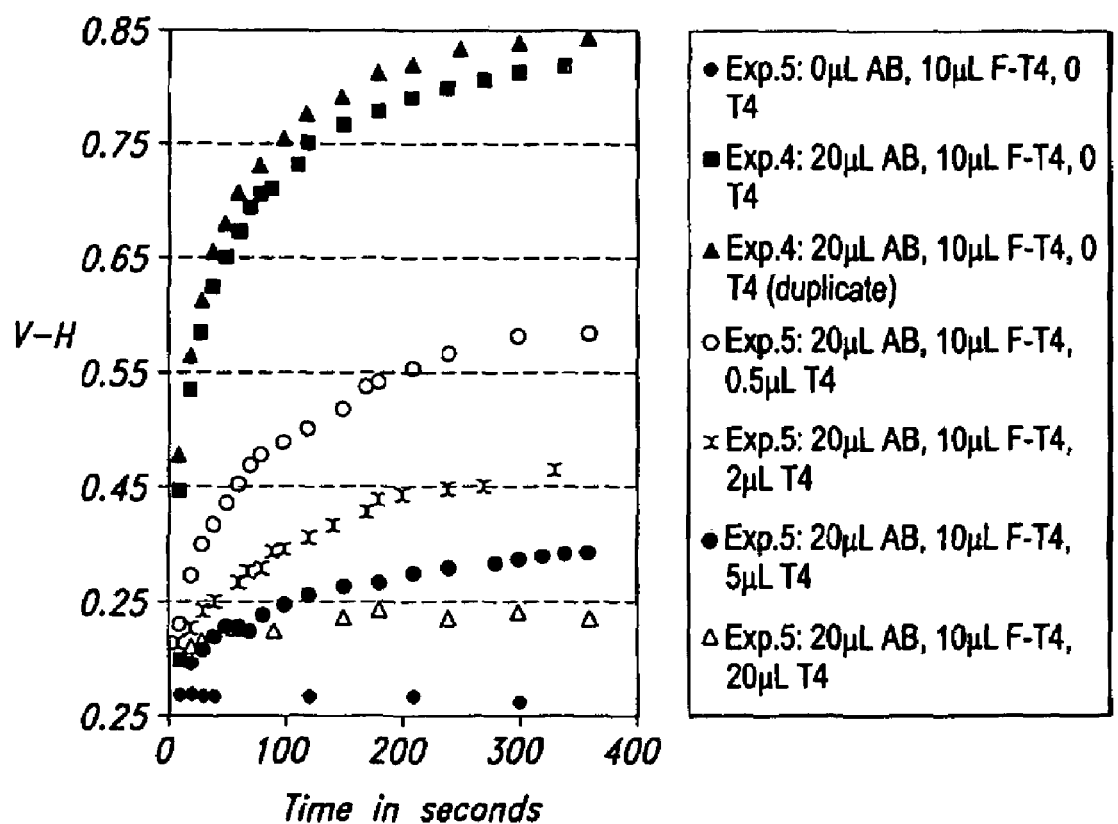
FIG. 1 is a graph of the results of competitive inhibition of the binding of F-thyroxine to its specific antibody by unlabeled thyroxine (T4).

The present invention provides an improved competitive assay for the detection and/or measurement of an analyte in a sample. The improvement to previous technology is that non-physiological amounts of one or more additives selected from salts, alcohols, solvents or combinations thereof are added to a reaction mixture in a sufficient amount to lower the rate of a specific macromolecular binding reaction. The term "additives" as used herein is intended to include, but is not limited to, chaotropes, cosmotropes, salting-in and salting-out agents as outlined by the Hofmeister series[1], organic salts, inorganic salts, non-ionic organic compounds, organic solvents and/or combinations thereof.

[1]Hofmeister F: Zur Lehre von der Wirkung der Salze. Arch Exp Pathol Pharmakol 1888, 24:247-260.

The reaction mixture includes a fluorescent conjugate of an analyte of interest. The reaction mixture also includes a component capable of specifically binding to the fluorescent conjugate in a specific binding reaction (i.e., the specific binding component). In some embodiments, the fluorescent conjugate is first exposed to its specific binding component. Then, a study of the inhibition of the binding of the fluorescent conjugate by a sample thought to contain the analyte of interest is performed. The assay is done in salt media. Inhibition of the binding of the fluorescent conjugate to its specific binding component is a function of the amount of analyte in the sample.

The specific binding component is capable of specifically binding to the analyte and its fluorescent conjugate. As described above, in some embodiments, the fluorescent conjugate is first allowed to interact with the specific binding component, followed by the addition of a sample thought to contain the analyte of interest. However, in other embodiments, the specific binding component is first allowed to interact with the analyte in the sample, followed by the addition of the fluorescent conjugate of the analyte. In still further embodiments, the specific binding component is allowed to simultaneously interact with the fluorescent conjugate of the analyte and the analyte in the sample.

As described above, before the present invention, it was necessary to combine fluorescence polarization and/or fluorescence intensity methods with stopped-flow methods in order to study fast reactions, and to measure initial and/or differential rates, which are usually very fast. The use of at least one additive in non-physiological amounts in the method of the present invention lowers the rate of the association reaction between the fluorescent conjugate and its specific binding component so that appropriate "slow" kinetics and hand mixing can be utilized. Therefore, the need for using stopped-flow or sophisticated mixing techniques is minimized or eliminated. This significantly simplifies assays for the detection and/or measurement of an analyte of interest, since only hand mixing and a direct "static" readout polarometer are needed.

The terms "lowering the rate", "lower the rate", "lowering the rate constant", "lower the rate constant", and the like as used herein is the lowering of the rate of the association reaction between the fluorescent conjugate and its specific binding component in the presence of a non-physiological amount of at least one additive, as compared to in the absence of a non-physiological amount of the additive. In particular, conducting the reaction in salt media decreases the rate constants of association reactions from about $10^7$-$10^8$ $M^{-1}$ $sec^{-1}$ or greater to between $10^4$-$10^6$ $M^{-1}$ $sec^{-1}$ or less. This allows the investigator to analyze a real sample by using fluorescence polarization and/or fluorescence intensity methods without stopped-flow. When lowering the rate constant, the concentration of the reactants can be increased and the reaction rate can still be slow enough to be measured with a "static" fluorescence polarometer, with increased sensitivity and specificity. Even stopped-flow devices will achieve enhanced sensitivity.

In some embodiments, the method of the present invention is a competitive inhibition-type kinetic assay. The method is useful for detecting and/or measuring unknowns. For example, the kinetic assay is useful for the detection of a hapten or antigen in a sample. In one embodiment, the substance to be detected is a low molecular weight organic substance or contaminant of environment concern. Such contaminants may be in a food or soil sample, for example. In another embodiment, the substance to be detected is a biological substance in a patient sample, e.g., blood or serum.

In some embodiments, a competitive inhibition rate assay of the present invention employs a fluorescent conjugate of the substance (analyte) of interest, together with an antibody to the analyte. In some embodiments, the antibody is first exposed to the fluorescent-labeled form of the analyte. Then, a study of the inhibition of the binding of this fluorescent conjugate by a sample thought to contain the analyte of interest is performed. The assay is done in the presence of non-physiological amounts of at least one additive.

In particular, the present invention provides methods of lowering the rate of a reaction in an assay for the detection and/or measurement of an analyte in a sample. One method includes:
  (a) providing a reaction mixture including at least two components selected from (i) a fluorescent conjugate of the analyte; (ii) a component capable of specifically binding to the analyte and its fluorescent conjugate; and (iii) a sample, which includes or is suspected to include the analyte;
  (b) providing the component not selected in step (a):
  (c) allowing the selected components in the reaction mixture to interact;
  (d) adding non-physiological amounts of at least one additive to the reaction mixture or the component of step (b) or both;
  (e) combining the reaction mixture and the step (b) component; and
  (f) monitoring for the rate of change of the concentration of a complex formed due to the combination of the components in step (a) and (b) to determine the concentration of the analyte in the sample.

The present invention also provides a method of lowering the rate of a reaction in an assay for the detection and/or measurement of an analyte in a sample that includes:
  (a) providing (i) a fluorescent conjugate of the analyte; (ii) a component capable of specifically binding to the analyte and its fluorescent conjugate; and (iii) a sample, which includes or is suspected to include the analyte;
  (b) allowing component (ii) to interact with the fluorescent conjugate of the analyte and the analyte in the sample, thereby forming a detectable complex due to the reaction between the fluorescent conjugate of the analyte and component (ii), wherein the reaction is performed in the presence of non-physiological amounts of at least one additive; and
  (c) monitoring for the rate of change of the concentration of the complex formed in (b) to determine the concentration of the analyte in the sample.

In some embodiments, the invention provides a method for lowering the rate of a specific binding reaction in an assay for sample analysis. This method includes providing a fluorescent conjugate of an analyte of interest; and providing a component that specifically binds to the analyte and its fluorescent conjugate. The method further includes providing a sample which includes or is suspected to include the analyte of interest, and allowing the fluorescent conjugate to react with its specific binding component in a specific binding reaction in the presence and absence of the sample. Significantly, the method also includes adding non-physiological amounts of at least one additive before binding to lower the rate of the specific binding reaction. The method also involves monitoring for the inhibition of the binding of the fluorescent conjugate to its specific binding component as a function of the amount of analyte in the sample.

In some embodiments of the methods of the present invention, the monitoring step can include measuring the rate of binding or the binding of the fluorescent conjugate to its specific binding component and determining the extent of inhibition of this binding by different known quantities of unlabeled analyte. The monitoring step can also include constructing a standard curve which shows the rate of binding by the fluorescent conjugate as a function of the quantity of the unlabeled analyte. The amount of analyte in the sample can then be determined by measuring the rate of binding or the binding of the fluorescent conjugate to its specific binding component in the presence of the sample and determining the amount of analyte in the sample from the standard curve.

In one embodiment, the additive decreases the rate constant of reaction from about $10^8$-$10^7$ $M^{-1}$ $sec^{-1}$ or greater to about from $10^6$-$10^4$ $M^{-1}$ $sec^{-1}$. In another embodiment, an association rate constant for the specific binding reaction of the fluorescent conjugate with its specific binding component decreases upon the addition of the non-physiological amounts of the additive.

In one embodiment, the additive is present in the assay in an amount of about 0.2 M to about 2.5 M. In another embodiment, the additive is present in an amount of about 5% to about 20% (weight/volume) of the reaction mixture.

Suitable additives include salts of an anion selected from the following: chloride, bromide, iodide, salicylate, trichloroacetate, thiocyanate, perchlorate and benzoate. In some embodiments, the additive is selected from the following agents: 8-anilino-1-napthalene-sulfonic acid, 2-Guanidinobenzimidazole, 2,3,5-triacetylguanosine, Benzimidazolylurea, acetamide, 2,2'-azino-bis(3-ethylbenzthiazoline-6-sulfonic acid), sodium trichloroacetate, sodium deoxycholate, creatine benzimidazole, sodium p-toluene-sulfonate, sodium dichloroacetate, sodium iodide, sodium fluoride, sodium chloroacetate, 5-benzimidazolecarboxylic acid, Salicylamide, guanidine hydrochloride, sodium chloride, 2-benzimidazole-proprionic acid, 2-benzimidazolemethanol, Sodium chlorodifluoroacetate, 4-guanidinobenzoic acid, 3-chlorobenzoic acid, N-hydroxy succinimide, guanidine and Potassium benzoate. The present inventors have found that, when present in non-physiological amounts, these additives lower the rate of the specific binding reaction, but otherwise do not significantly disturb the specific binding reaction. Non-physiological amounts of the salt agents include ranges of 0.2 M to 2.5 M, desirably 0.3 M to 2.0 M, more desirably 0.4 M to 2.5 M and even more desirably 0.5 M to 1.5 M.

However, the upper limit of salt concentration may go beyond these ranges provided that it does not have deleterious effects on the assay and is largely dictated by practical considerations, such as unwanted precipitation and/or denaturation of reaction components, excessive precipitation of salts, general interference with the results, among other practical considerations.

In one embodiment, the additive affects the order of reaction with respect to the first component and the second component in the reaction mixture. In one preferred embodiment, the additive makes the binding reaction first order with respect to the concentration of each of the first and second components. This allows the investigator to follow a simple biomolecular reaction between the first and second components. This is described in further detail below.

The method of the present invention employs a fluorescently-labeled conjugate of the analyte of interest. Use of a fluorescent label allows the methods of the present invention to be carried out either by fluorescence polarization measurements or, in some cases, by fluorescence intensity measurements. In one preferred embodiment, a method of the present invention is a fluorescence polarization assay.

As described above, an increase in fluorescence polarization or a change in fluorescence intensity via enhancement or quenching of a fluorescent reactant usually occurs during the combination with its macromolecular partner. An increase in polarization reflects a slowing down of the rotary motion of the fluorescent reactant when it becomes attached to its macromolecular partner. This increase in fluorescence polarization occurs even if there are no concomitant changes in the fluorescent intensity. In the method of the present invention, the fluorescent conjugate (tracer) competes with the analyte in the sample for the antibody. The fluorescent conjugate will only exhibit polarized fluorescence when bound to the antibody, and this will be inversely proportional to the concentration of the analyte in the sample.

In the methods of the present invention, equilibrium fluorescence polarization and intensity measurements can be made in a direct readout "polarometer". Moreover, kinetic measurements of "slow" kinetic processes (10 seconds or greater), where the reaction is carried out in salt media, can be made in a direct readout polarometer.

Polarometer denotes an instrument for measuring the degree of polarization as contrasted to optical rotation. The solution to be measured is first excited in a standard cell by linearly polarized light of appropriate wavelength. The emission fluorescent beam (with appropriate filters) then passes through a rapidly rotating polarizer and onto a photomultiplier tube whose output is fed into a computer which calculates the fluorescence polarization, p=(V−H)/(V+H), Polarized Fluorescence Intensity Difference or PFID (V−H), and the total fluorescence intensity, V+H. V and H denote intensities of vertically polarized and horizontally polarized components in fluorescent light. Alternatively, a "T-format" polarometer using two photomultiplier tubes set at right angles to the excitation source and each having polarizing filters place in a mutually orthogonal position. Provision is made for automatic deduction of the blank. Temperature control of the cell compartment is maintained with an appropriate thermostat.

Direct readout polarometers are available commercially. For example, such instruments are available from the following vendors: BMG Labtech GmbH, Offenburg, Germany; JASCO Corporation, Tokyo, Japan; Tecan Schweiz AG, Hännedorf, Switzerland; Bioscan, Inc, Washington, D.C.; Molecular Devices Corporation, Sunnyvale, Calif.; Perkin Elmer Life and Analytical Sciences, Inc., Wellesley, Mass.; Photon Technology International, Inc., Birmingham, N.J.; Abbott GmbH & Co KG, Wiesbaden, Germany; Daichemix Corp. (USA), Witefishbay, Wis.; and Invitrogen Corp., Carlsbad, Calif.

As described above, the inherent sensitivity of fluorescence measurements can be used in monitoring the extent of reaction as a fluorescent reactant, F, combines with its macromolecular partner, R:

$$F + R \underset{k_{-1}}{\overset{k_1}{\rightleftharpoons}} F-R \qquad \text{Eq. (1)}$$

where $k_1$ is the forward reaction and $k_{-1}$ is the back reaction such that $(k_1)(k_{-1})=K_{(eq)}$.

The ratio of bound to free fluorescent material in Eq. (1) above can be directly related to fluorescence polarization and intensity parameters, as shown in the equations below (Dandliker, et al, (1969) Immunochemistry, 6, 125):

$$\frac{F_b}{F_f} = \frac{Q_f}{Q_b}\left(\frac{P-P_f}{P_b-P}\right) \qquad \text{Eq. (2)}$$

$$\frac{F_b}{F_f} = \frac{Q_f - Q}{Q - Q_b} \qquad \text{Eq. (3)}$$

In equations (2) and (3) above, the symbols or subscripts are as follows: f and b, denote free and bound forms, respectively; p denotes the polarization of fluorescence; F denotes fluorescent-labeled material; and Q denotes the ratio of fluorescence intensity to molar concentration of fluorescent-labeled material.

If the binding sites on the fluorescent reactant's macromolecular partner are uniform, the results can be treated by the Scatchard form of the mass law, $$\frac{F_b}{F_f} = K(F_{b,max} - F_b) \qquad \text{Eq. (4)}$$

where $F_{b,max}$ is the maximum value of $F_b$ and is taken to be equal to the initial binding site concentration of R. R in equation 4 is equal to $(F_{b,max}-F_b)$. K is the association constant for the reaction and the sum, $F_b+F_f=M$, is the known concentration of fluorescent reactant.

The interpretation of kinetics in terms of fluorescence polarization was carried out by initial rate equations:

$$\left(\frac{dF_b}{dt}\right)_0 = -\left(\frac{dF_f}{dt}\right)_0 = \frac{Q_f}{Q_b}\left(\frac{F_{f,0}}{P_b - P_f}\right)\left(\frac{dP}{dt}\right)_0 \qquad \text{Eq. (5)}$$

$$\left(\frac{dP}{dt}\right)_0 = \frac{Q_b}{Q_f}(P_b - P_f)k(F_{b,max})(N_1)(F_{f,0})(N_2 - 1) \qquad \text{Eq. (6)}$$

where k is the usual second order rate constant For constant $F_{b,max}$ but varying $(F_f)_o$ $$\log\left(\frac{dP}{dt}\right)_0 = (N_2 - 1)\log(F_{f,0}) + \text{constant} \qquad \text{Eq. (7)}$$

Alternatively, for constant $(F_{f,o})$, but varying $(F_{b,max})$:

$$\log\left(\frac{dP}{dt}\right)_0 = (N_1)\log(F_{b,max}) + \text{constant} \qquad \text{Eq. (8)}$$

In the kinetic equations, P is the value of the polarization, $N_2$ is the order of the reaction with respect to the fluorescent reactant concentration, and $N_1$ that with respect to the concentration of binding sites on its macromolecular partner. The subscript "0" refers to zero time. Equations (7) and (8) are especially useful in determining the order of a reaction, which is an important characteristic to establish when investigating kinetic relationships. If the order with respect to the concentration of each reactant proves to be constant over a wide concentration range, then it is likely that the path of the reaction is also remaining the same which gives some assurance that derived kinetic constants have some simple physical meaning. Also, equations (7) and (8) are in a form easy to use, since it is not necessary to know the absolute but only the relative concentrations of each reactant. Dealing with initial rates while focusing only upon the initial stages of reaction accomplishes some simplification by avoiding the back reaction.

In some embodiments of the present invention, a nonphysiological amount of a suitable additive can affect the order of the reaction with respect to the fluorescent conjugate (e.g., fluorescently-labeled analyte) and its specific binding component (e.g., antibody). In one example, the additive makes the binding reaction first order with respect to the concentration of each of the fluorescent conjugate and its specific binding component (i.e., $N_1$ in Eq. 8 and $N_2$ in Eq. 7 will each be 1).

As described above, there are situations where fluorescence polarization and intensity measurements can not be made without stopped-flow techniques. For example, when there is a fast reaction (rate is $10^7 M^{-1} sec^{-1}$ or greater), it is not easy to measure p, V−H and V+H in a direct readout polarometer without also using a stopped-flow device. This is described further in the examples below. The present invention is directed to simplifying the instrumentation necessary to obtain P, V−H and V+H measurements for "fast" reactions by employing a non-physiological amount of at least one additive in the reaction mixture. The additive allows for appropriate "slow" kinetics and hand mixing. Therefore, conducting the assay in salt media allows the investigator to use only a direct readout polarometer for measurements. Preferably, the additive is present in an amount of about 0.5 M to about 1.5 M or higher.

The competitive-type assay of the present invention is preferably a fluorescence polarization assay. In one desired embodiment, the monitoring step involves monitoring for a change in the initial rate of polarized fluorescence intensity difference (PFID), defined as the absolute difference in the polarized fluorescence in the vertical and horizontal directions (i.e., V−H) as a function of an amount of analyte in the sample. For example, the rate change in V−H (PFID) is measured before and then after the sample is added, and the difference between these rate values over a set time period is calculated. The rate change in PFID is then compared to a standard curve to determine the amount of analyte. Such a standard curve is constructed by monitoring for a change in the rate as a function of different known quantities of unlabeled analyte. The amount of analyte in the sample can be determined from the standard curve. It should be mentioned that this invention is not limited to only the use of initial rate equations, where t approaches 0. Equation 5 can be generalized in the form of a differential rate expression at time=t.

$$\left(\frac{dF_b}{dt}\right)_t = k(RF_f) = \frac{1}{(Q_b - Q_f)}\left(\frac{d[V+H]}{dt}\right), \text{ where} \qquad \text{Eq. (9)}$$

$$\frac{[V+H]}{M} = Q$$

$$= \frac{1}{(Z_b - Z_f)}\left(\frac{d[V-H]}{dt}\right), \text{ at time } t$$

$$= \frac{F_f\left(\frac{Q_f}{Q_b}\right)\left[\frac{(P_b - P_f)}{(P_b - P)^2}\right]\left(\frac{dP}{dt}\right)}{1 + \left(\frac{Q_f}{Q_b}\right)\frac{(P - P_f)}{(P_b - P)}}$$

The kinetic investigator, depending on immunoassay conditions, can choose to measure the tangents to the rate curves and use the following definitions: (time=t)

$$P=P_t; (V-H)=(V-H)_t; (V+H)=(V+H)_t \qquad \text{Eq. (10)}$$

and use these definitions with appropriate computational methods to determine the differential rate.

The particular fluorescent moiety chosen to form the conjugate with the analyte is selected from any number of fluorescent moieties. The choice of fluorescent moiety is to a large extent a matter of convenience once a coupling chemistry has been selected. Virtually any fluorophore having a fluorescence lifetime of between 0.1 and 50 nanoseconds and having an excitation wavelength of 350 to 800 nanometers is suitable for purposes of the present invention. For a detailed listing of fluorophores, which are commercially available, see Handbook of Fluorescent Probes and Research Chemicals, ed. Karen Larison, by Richard P. Haugland, Ph.D., 5$^{th}$ ed., 1992, published by Molecular Probes, Inc. Some examples of suitable fluorescent moieties include the following: 7-AAD, Acridine Orange, Alexa 488, Alexa 532, Alexa 546, Alexa 568, Alexa 594, Aminonapthalene, Benzoxadiazole, BODIPY 493/504, BODIPY 505/515, BODIPY 576/589, BODIPY FL, BODIPY TMR, BODIPY TR, Carboxytetramethylrhodamine, Cascade Blue, Coumarin, CY2, CY3, CY5, CY9, Dansyl Chloride, DAPI, Eosin, Erythrosin, Ethidium Homodimer II, Ethidium Bromide, Fluorescamine, Fluorescein, FTC, GFP (e.g. yellow shifted mutants T203Y, T203F, S65G/S72A), Hoechst 33242, Hoechst 33258, IAEDANS, Indopyras Dye, Lanthanide Chelate, Lanthanide Cryptate, Lissamine Rhodamie, Lucifer Yellow, MANT, MQAE, NBD, Oregon Green 488, Oregon Green 514, Oregon Green 500, Phycoerythrin, Porphyrin, Propidium Iodide, Pyrene, Pyrene Butyrate, Pyrene Maleimide, Pyridyloxazole, Rhodamine 123, Rhodamine 6G, Rhodamine Green, SPQ, Texas Red, TMRM, TOTO-1, TRITC, YOYO-1, Vitamin B12, flavin-adenine dinucleotide, 6-carboxy-X-rhodamine, nicotinamide-adenine, and dinucleotide. Preferably, the fluorescent conjugate would have a fluorescent wavelength different from competing fluorescent substances which may occur in host samples of interest, e.g., blood, serum, urine, tissue and extracts thereof.

In one embodiment, the analyte of interest is an organic contaminant. The organic contaminant can be one of environmental concern. For example, in one embodiment, the organic contaminant is a fungal or microbial toxin. Other analytes that can be detected with a method of the present invention include, but are not limited to, drugs, steroids, hormones, proteins, peptides, lipids, sugars, receptors, nucleic acids, vitamins, etc. For example, in one embodiment, the analyte of interest is thyroxine, which is a major hormone secreted by the follicular cells of the thyroid gland.

In some embodiments, the component that specifically binds to the analyte of interest is an antibody. It is well known that a substance, when injected into an animal, stimulates the animal to produce antibody. The antibody is capable of reacting with the injected substance in a highly specific manner. These antibodies belong to a group of serum proteins known as immunoglobulins. The production of these antibodies as a result of the injection of the antigen takes place over a period of many weeks, and depends upon the immunization schedule. In general, "good" antigens are usually of large molecular size (greater than 20,000 MW), partially digestible by enzymes and are recognized as being foreign by the antibody-producing animal.

Many compounds of environmental concern do not have a large molecular weight, and would, therefore, appear to be incapable of stimulating antibody formation. However, this is not the case. So-called partial antigens or haptens can be produced and are capable of reacting with specific antibody. Haptens or partial antigens are defined as antigens which alone cannot induce antibody formation, but in conjugation with a suitable carrier can produce antibody against themselves, as well as against the carrier-hapten complex. Example of carriers include ovalbumin, bovine serum albumin, fibrinogen, and many others. Conjugation may be carried out by methods known in the art (Coligan, J. E. et al. (Eds.) Current Protocols in Immunology, Chapter 9, Wiley Intersciences, New York, 1999).

The hapten, once conjugated with a suitable carrier, can stimulate antibody production. Some antibody will be produced which is highly specific in its reaction with the hapten alone. Therefore, by employing hapten-specific antibodies, the methods of the present invention can be used in the detection and quantitation of even low molecular weight organic compounds, such as pesticides.

Antibodies suitable for use in the methods of the present invention include polyclonal and monoclonal antibodies. Polyclonal antibodies can be prepared in accordance with known methods (Coligan, J. E, et al. (Eds.), Current Protocols in Immunology, Wiley Intersciences, New York, 1999).

Monoclonal antibodies may be produced by methods known in the art. These methods include the immunological method described by Kohler and Milstein in Nature 256:495-497 (1975) and by Campbell in "Monoclonal Antibody Technology, The Production and Characterization of Rodent and Human Hybridomas" in Burdon et al. (ads.), Laboratory Techniques in Biochemistry and Molecular Biology, Volume 13, Elsevier Science Publishers, Amsterdam (1985); and Coligan, J. E, et al. (Eds.), Current Protocols in Immunology, Wiley Intersciences, New York, (1999); as well as the recombinant DNA method described by Huse et al., Science 246: 1275-1281 (1989).

Antibodies against markers in normal human tissue and neoplasms are commercially available, for example, from Invitrogen Corporation (Carlsbad, Calif.), Advanced Immunochemical Inc. (Long Beach, Calif.) and RDI Division of Fitzgerald Industries, Intl. (formerly Research Diagnostics, Inc., Concord, Mass.). These include, but are not limited to, monoclonal and polyclonal antibodies against the following classes of analytes: proteins (e.g., enzymes, growth factors, cytokines), peptides, receptors (e.g., CD markers), toxins, infectious agents (e.g., viruses), steroids, hormones, lipids and lipoproteins). For example, antibodies against angiogenesis markers are commercially available, and such antibodies include those against the following receptors: CD31, CD34, Vascular Endothelial Growth Factor (VEGF), Vascular Endothelial Growth Factor C (VEGF-C) and Vascular Endothelial Growth Factor Receptor 3 (VEGFR-3). Also, antibodies against cancer markers are commercially available, such as those against the following: ALK, ALK 400, c-kit (CD117), COX-1, COX-2, EZH2, Ezrin, MAGE-A, Mesothelin, MTA1, NY-ESO-1, PDEF, PRAC, PSMA, RCAS1, thymidylate synthase and tyrosinase. Furthermore, antibodies against markers for specific types of cancer are commercially available. For example, commercially available antibodies against breast cancer markers include those against the following: BCA-225, Bcl-2, c-Met, Cathepsin D, CD63, cytokeratins, E-cadherin, EGFr, estrogen receptor, progesterone receptor, HER2, HER4, p53 and phospho-MAP kinase. Moreover, markers for colon cancer include, but are not limited to, CA 19-9, CEA, COX-1, Ezrin, MLH1, MSH2, MSH6, Platelet Derived Endothelial Cell Growth Factor (PD-ECGF), PRLr and Thymidylate Synthase (TS). Antibodies against these colon cancer markers, as well as markers for other specific cancers, diseases or disorders are also commercially available.

Antibodies against apoptosis markers are also commercially available, and these markers include, for example, Bax, Bcl-2, Bcl-XL and PARP. Moreover, antibodies against cell cycle and cell proliferation markers are commercially available. Such cell cycle and cell proliferation markers include, but are not limited to, BrdU, Cyclin D1, Cyclin E, p21, Proliferating Cell Nuclear Antigen (PCNA) and S-Phase Kinase-Associated Protein 2 (SKP2). Antibodies against cellular proteins, such as, but not limited to, calcitonin, HLA DR, MGMT, nitrotyrosine and nNOS are also commercially available. Moreover, antibodies against cytoskeletal proteins, such as α-Tubulin, β-Tubulin, Actin, Desmin, GFAP, Myosin, Ubiquitin and Vimentin, are commercially available. Furthermore, antibodies against markers for lipoprotein metabolism are commercially available. Such antibodies include, for example, those against HDL, LDL, APOE, ApoE2, LDL receptors, etc. The abbreviations used herein for the markers are well known in the art.

Furthermore, antibodies against pesticides and herbicides are commercially available from such companies as Guildhay, Ltd. (Guildford, Surrey, England). For example, antibodies against 2,4-D, aldrin, atrazine, chlortoluron, diuron, isoproturon, MCPA, mecoprop, paraquat, simazine, solanine, etc. are commercially available.

The present invention is not, in any way, limited to the specific examples provided herein of analytes and antibodies that specifically bind to the analytes.

In other embodiments of the present invention, the component that specifically binds to the analyte is a receptor. For example, if a hormone carrying a fluorescent label attaches to its receptor, the hormone is thereby largely immobilized and this immobilization is registered by an increase in the polarization of the emission from the attached fluorescent label.

In addition to antigen-antibody, hapten-antibody and hormone-receptor interactions, the methods of the present invention can also be applied to enzyme-substrate, protein-DNA, peptide-antibody and ligand-receptor interactions.

Table A below provides some further examples of analytes, which may be detected and/or measured using the methods of the present invention. In some embodiments, a fluorescent conjugate of the analyte can be employed in methods of the present invention. The analysis may be performed, for example, in water, serum, blood, urine or other bodily fluids. Moreover, the analysis may be performed in milk, wine, juices and food extracts. Table A is for illustrative purposes only and is not intended to limit the scope of the present invention.

TABLE A

| CLASS | EXAMPLES |
|---|---|
| Pesticides | Acetochlor and Other Acetanilides, atrazin, simazine, triazine, 2,4-D, 2,4,5-T, dichlorprop, MCPA, MCPB, Triclopyr, Pentachlorophenol, DDT, Isoproturon, Methabenzthiazurone, Metasulfuron-methyl, Chlorsulfuron, Acetochlor, Propanil, Paraquat, Parathion-methyl, BTEX, Nonylphenol, LAS |
| Lipids | DHET |
| Sugars | Bacterial sugars, polysaccharides |
| Peptides, Proteins, Receptors | IGG, Albumin, Receptors, KLH, LPH Myoglobin, Feto proteins, AT1 |
| Oligonucleotides, DNA, RNA | Bacterial, animals, plants, specific sequences |
| Toxins | Zearalenone, Deoxynivalenol, T-2, Aflatoxins, Ochratoxin, Fumonisins, Patulins, Trichothecene, citrinin, Cyclopiazonic acid, monoliformin, sterigmatocystin, alternaria-mycotoxins, ergot alkaloids |
| Vitamins | B 12, Vitamin C, Folic acid |
| Small Molecules | Chlorinated compounds, metals |
| Therapeutic drugs, e.g., antiasmatics, antineoplastics, | Theophylline, doxorubicin, methotrexate, disopyramide, lidocaine, procainamide, propranolol, quinidine, N-acetyl- |

TABLE A-continued

| CLASS | EXAMPLES |
| --- | --- |
| antiarythmics, anticonvulsants, antibiotics, antiarthritics, antidepressants, etc. | procainamide, Phenobarbital, phenotoin, pridon, valproic acid carbamazepine, ethosuximide, cephalosporins, erythromycin, tetracyclin, vancomycin, gentamicin, amikacin, chloramphenicol, streptomycin, tobramycin, penicillin, salicylate, nortriptyline, amitriptoline, imipramine, desipramine, liodcaine, histamine, thyroxin, triiodothyronine, serotonin, etc. |
| Drugs of abuse | Morphine, heroin, hydromorphone, dihydrocodeine, pholcodine, Amphetamine, etc. |
| Steroids and hormones | Esterone, estradiiol, cortisol, testosterone, progesterone, chenodeoxycholic acid, digoxin, cholic acid, digitoxin, deoxycholic acid, lithocholic acid, etc. |
| Prostaglandins | PGE, PGF, PGA others |
| Components of binding and reaction studies | Antibodies, receptors, enzymes (i.e., proteases, nucleases, phosphatases) |

In one embodiment of the present invention, the component that specifically binds to the analyte and its fluorescent reactant is on a solid substrate. For example, a specific binding component, such as an antibody, can be deposited on a glass, plastic or paper substrate. Substrates can include various microporous filters, such as PVDF filters, nitrocellulose filters, cellulosic filters and the like. In one example, the antibody can first be bound to a substrate, such as PVDF. Second, the antibody on the substrate can be exposed to a fluorescent-labeled form of an analyte of interest. Then, a study of the inhibition of the binding of this fluorescent conjugate by a sample thought to contain the analyte of interest is performed. In particular, one can observe a change in p, V–H and/or V+H which occurs in the presence of the sample.

The competitive-inhibition assay of the present invention can be applied to the simultaneous analysis of multiple analytes in a sample using analytes labeled with different fluorescent wavelength conjugates. This would reduce the time and effort involved in multi-analyte, multi-sample analyses.

The following examples are for illustrative purposes only, and are not to be construed as limiting the present invention.

EXAMPLES

Example 1

Materials

Preparation of Buffers

The influence of at least one additive on a reaction occurring between specific binding molecules was investigated in pH 7.5 buffer solutions. These buffer solutions were denoted "Buffer 1" and "Buffer 2" and each contained a different amount of sodium benzoate.

Buffer 1:
0.5 M sodium benzoate in Phosphate Buffered Saline (PBS), adjusted to pH 7.5. The final concentration of sodium benzoate in buffer 1 was about 7.2% w/v.

Buffer 2:
1.0 M sodium benzoate in PBS, adjusted to pH 7.5. The final concentration of sodium benzoate in buffer 2 was about 14.4% w/v.

Preparation of Anti-Sera Stock Solution
An initial stock solution of anti-thyroxine sera was prepared. In particular, 1 ml of polyclonal anti-thyroxine sera containing 10 mg/ml IgG (Sigma) was diluted 1:5 in PBS buffer, pH 7.5. The final concentration of IgG in the stock solution was about 2 mg/ml.

Preparation of Thyroxine Stock Solution
An initial stock solution of an analyte (thyroxine) was prepared. Unlabeled thyroxine at 1 mg/ml in 0.5 M NaOH was diluted 100-fold in PBS. The final concentration of thyroxine in the stock solution was about 10 µg/ml.

Preparation of Fluorescein-Labeled Thyroxine Stock Solution
An initial stock solution of fluorescein-labeled analyte (F-thyroxine) was prepared. Fluorescein-labeled thyroxine at 1248 g/mol in a lyophilized form was obtained from emp Biotech GmbH. First, 5 mg ($4 \times 10^{-6}$ moles) of F-thyroxine was diluted to 10 ml in PBS to get a $4.1 \times 10^{-4}$ M solution of F-thyroxine. This solution was then further diluted 100-fold in PBS. The final concentration of F-thyroxine in the stock solution was about $4.1 \times 10^{-6}$ M.

Example 2

Kinetic Curve Measurement Methodology

The following is a protocol useful for performing a fluorescein polarization assay of the present invention. All steps are performed at ambient temperature. The total final reaction volume after all additions is 3030 µl.

1. Add 20 µl or 0 µl (control) anti-sera stock solution to about 2980 µl of Buffer 1.
2. Pipette the diluted anti-sera solution prepared in step 1 up and down from 1 to 10 seconds to thoroughly mix.
3. Add between 0 and 20 µl thyroxine stock solution (e.g., 0, 0.5, 2.0, 5.0 and 20 µl) to the mixed anti-sera from step 2.
4. Pipette the mixture formed in step 3 up and down for 1 to 10 seconds and then incubate for 30 to 300 seconds.
5. Add 10 µl of the Fluorescein-labeled thyroxine stock solution to the incubated mixture from step 4.
6. Pipette the mixture formed in step 5 up and down for 1 to 10 seconds and begin measuring polarization (P), Polarized Fluorescence Intensity Difference (V–H) or quenching (V+H total intensity) versus time for between 10 and 7200 seconds after end of mixing in a direct readout polarometer or between 0.1 and 7200 seconds after end of mixing with a stopped-flow polarometer.
7. Determine the rate of reaction (initial rates) and plot versus amount of thyroxine stock solution added in step 3 to produce a standard curve.
8. Against a standard curve, an unknown amount of thyroxine can be measured by comparison of initial rate measurement (speed of reaction) of unknown with the standard curve.

Example 3

Kinetic Curve Measurable in the Presence of an Additive Using a Fluorescein-Labeled Thyroxine/Anti-Thyroxine System This example demonstrates that a reaction between F-thyroxine and its specific antibody was only capable of being followed when the reaction was performed in the presence of an additive. The additive in the present example was sodium benzoate. The thyroxine/anti-thyroxine system is well known to be a very difficult system to measure due to thyroxine's capacity to bind to many things non-specifically. It was for this reason that the thyroxine-anti-thyroxine system was chosen as a model system to demonstrate the present invention.

The materials described in Example 1 and the protocol described in Example 2 were used for each of Experiments 1 to 5 shown in Table 1 below, except that for Experiments 1 to 3, the reaction was performed in PBS instead of Buffer 1. Experiment No. 1 is a control to establish baseline measurements for polarization (P), V−H, and V+H.

TABLE 1

| Experiment No. | Antiserum (µl) | Thyroxine (µl) | F-thyroxine (µl) | Additive |
|---|---|---|---|---|
| 1 | 0 | 0 | 10 | − |
| 2 | 20 | 0 | 10 | − |
| 3 | 20 | 20 | 10 | − |
| 4 | 20 | 0 | 10 | + |
| 5 | 20 | 20 | 10 | + |

Results of Experiment 1

Polarization, V−H and V+H were measured versus time for between 10 and 600 seconds. During this time period, fluorescence polarization baseline measurements were constant. In particular, V−H values were between 0.198 to 0.193 V, V+H values were between 2.135 to 2.130, and V and P values were between 91 to 90 mP.

Results of Experiment 2

Attempts were made to measure P, V−H and V+H versus time for between 30 seconds and 600 seconds. However, the reaction was immediate and the values obtained for P, V−H and V+H did not change over this time period. In particular, V−H was at 1.51 V, V+H was at 8.118, and V and P values were at 184 mP throughout the measurement period.

The results of Experiment 2 indicate that it was not possible to measure a kinetic curve in the absence of an additive. In particular, it was not possible to obtain meaningful information during the measurement of the reaction between the fluorescently-labeled thyroxine and its specific antibody in the absence of benzoate.

Results of Experiment 3

Attempts were made to measure P, V−H and V+H versus time for between 30 seconds and 600 seconds. However, the reaction was immediate and the values for P, V−H and V+H were constant over the measurement period. In particular, V−H was at 0.1580 V, V+H was at 5.243, and V and P values were at 30 mP throughout the measurement period.

The results of Experiment 3 indicate that it was not possible to obtain meaningful information during the measurement of a kinetic curve in absence of an additive due to non-specific binding. In particular, it was not possible to follow the binding between F-thyroxine and its specific antibody, nor the inhibition of this binding by the unlabeled thyroxine in the absence of benzoate.

Results of Experiment 4

Polarization, V−H and V+H values were measured for between 10 and 600 seconds. During this time course, a kinetic curve was obtained using an anti-thyroxine/F-thyroxine system, in which no unlabeled thyroxine was added. In particular, the polarization, V−H and V+H values increased during the 600 second time period.

The increase in polarization was due to the binding occurring between the F-thyroxine and its specific antibody. The results of Experiment 4, which are provided in FIG. 1, indicate that it was possible to obtain meaningful information during the measurement of a kinetic curve in the presence of an additive.

Results of Experiment 5

A study of the competitive inhibition of the binding of the F-thyroxine to its specific antibody by unlabeled thyroxine in the presence of sodium benzoate was performed.

The results of this competitive inhibition type assay of the present invention indicated that inhibition of the binding of F-thyroxine to its specific antibody by unlabeled thyroxine occurred. These results are shown in FIG. 1. In particular, in Experiment 5, a standard inhibition curve was obtained using various amounts of unlabeled thyroxine from 0 µl to 20 µl using the protocol in Example 2. This standard curve is used to measure unknown quantities of analyte. This also demonstrates it is possible to perform an immunoassay in the presence of an additive.

Example 4

Figure 2:
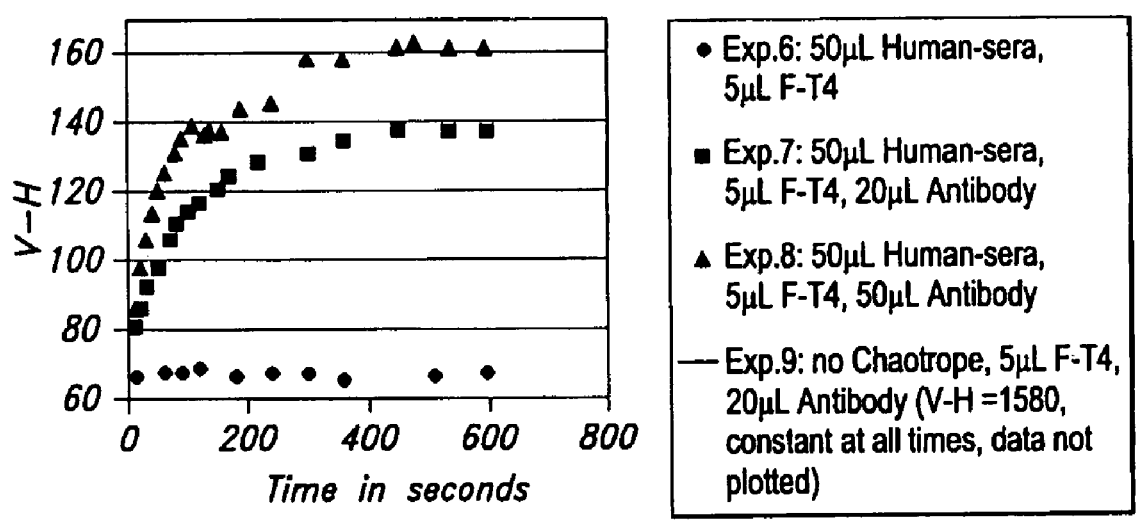
FIG. 2 is a graph of the effects of an additive on specific and non-specific binding.

Effects of an Additive on Specific and Non-Specific Binding in a F-Thyroxine/Anti-Thyroxine System With reference to FIG. 2, experiments were performed to determine the effects of an additive on specific and non-specific binding. The additive used in the present example was sodium benzoate. The materials described in Example 1 and the measurement methodology described in Example 2 were used. In particular, 50 µl of human sera was added to 3000 µl of Buffer 2 or PBS at pH 7.5 (no additive control) and thoroughly mixed by pipetting for 1 to 10 seconds. To this was added 0 µl of unlabeled thyroxine and 0 µl, 20 µl or 50 µl of anti-sera stock solution. The mixture was thoroughly mixed by pipetting for 1 to 10 seconds. Then, 5 µl of the fluorescein-labeled thyroxine stock solution was added. This was followed by mixing for 1 to 10 seconds by pipetting. Then, d(V−H)/dt measurements were made versus time for between 10 and 600 seconds. This protocol was followed for Experiments 6-9 in Table 2. This table shows the experimental set-ups, and the corresponding symbols used in FIG. 2 for each experiment.

TABLE 2

| Experiment No. | Antiserum (µl) | Human Sera (µl) | F-thyroxine (µl) | Additive |
|---|---|---|---|---|
| 6 (♦) | 0 | 50 | 5 | + |
| 7 (■) | 20 | 50 | 5 | + |
| 8 (▲) | 50 | 50 | 5 | + |
| 9 (-X-) | 20 | 50 | 5 | − |

Results

As shown in FIG. 2, it was only possible to measure an increase in PFID (V−H) values over the 600 second time course in the presence of an additive (▲ and ■). An increase in P and V+H values was also observed over this time course in the presence of the additive. V–H values did not change in the absence of the additive (—X—; data not shown).

The data further show that the reaction only proceeds in the presence of anti-sera (see constant V–H values for ♦, where no anti-sera was present). The overall results indicated that the additive inhibits non-specific binding, but does not inhibit specific binding.

Example 5

Kinetic Curve Measurable in the Presence of an Additive Using a Rhodamine-Labeled Thyroxine/Anti-Thyroxine System This example demonstrates the successful use of a non-fluorescein "red"-labeled thyroxine/anti-thyroxine system for fluorescence polarization and polarized fluorescence intensity difference PFID (V–H) measurements as a substitute system for a fluorescein-labeled thyroxine/anti-thyroxine system. The protocol used is described below. The additive was sodium benzoate combined with an organic solvent (5% isopropanol).
1. Use clean glassware, washed with isopropanol.
2. Make a 0.5 M solution of sodium benzoate.
3. Make a solution of 5% isopropanol in 0.5 M sodium benzoate (i.e., 2.5 ml 2-propanol in 47.5 mL 0.5 M aqueous sodium benzoate). This will be named BUFFER.
4. 800 µl of BUFFER added to approximately 200 µg 5-carboxy-X-rhodamine-thyroxine (ROX-T4). This will be named STOCK ROX-T4 solution.
5. 600 µl Buffer added to 1 mL cuvette. The absorbance spectrum is measured using a UV-VIS spectrophotometer, 400 nm to 800 nm. This spectrum is used to define the absorbance of the background as zero and to control that it is actually zero.
6. Add approximately 20 µl of STOCK ROX-T4 to cuvette and mix. Measure the absorbance UV-VIS, 400 nm to 800 nm. Absorbance maximum is measured to be 582 nm.
7. Using a rotating polarometer with a 75 watt Xenon short-arc lamp. The rotating polarizer has three channels: Polarization (P), Total Intensity (V+H), and V–H.
8. Add 2 µl STOCK ROX-T4 to 3000 µl (3 mL or 3 cc) BUFFER. Measure P, V+H and V–H after short mixing and 30 second equilibration. P=0.075; V+H=2291; V–H=178. Conclusions: Intensity has increased due to presence of more fluorophore; Polarization has remained constant because there is no binding.
9. Add 10 µl. Antibody solution (anti-thyroxine in PBS, dilution unknown, probably 5 mg in 1000 µl PBS and further diluted 1:10 in PBS). New volume is 3017 µl. Measure P, V+H and V–H after short mixing. Results are shown in Table 3 below;

TABLE 3

| Time(s) | P (mP) | V + H | V – H |
|---|---|---|---|
| 0 | 75 | 2291 | 178 |
| 10 | | | 660 |
| 13 | | | 860 |
| 18 | | | 936 |
| 20 | | | 1006 |
| 26 | | | 1130 |
| 30 | | | 1175 |
| 33 | | | 1200 |
| 44 | | | 1259 |
| 49 | | | 1280 |
| 53 | | | 1290 |
| 62 | 392 | | |

TABLE 3-continued

| Time(s) | P (mP) | V + H | V – H |
|---|---|---|---|
| 70 | 395 | | |
| 78 | | | 1345 |
| 83 | | 3375 | |
| 95 | 397 | | |
| 600 | 398 | 3320 | 1340 |

Figure 3:
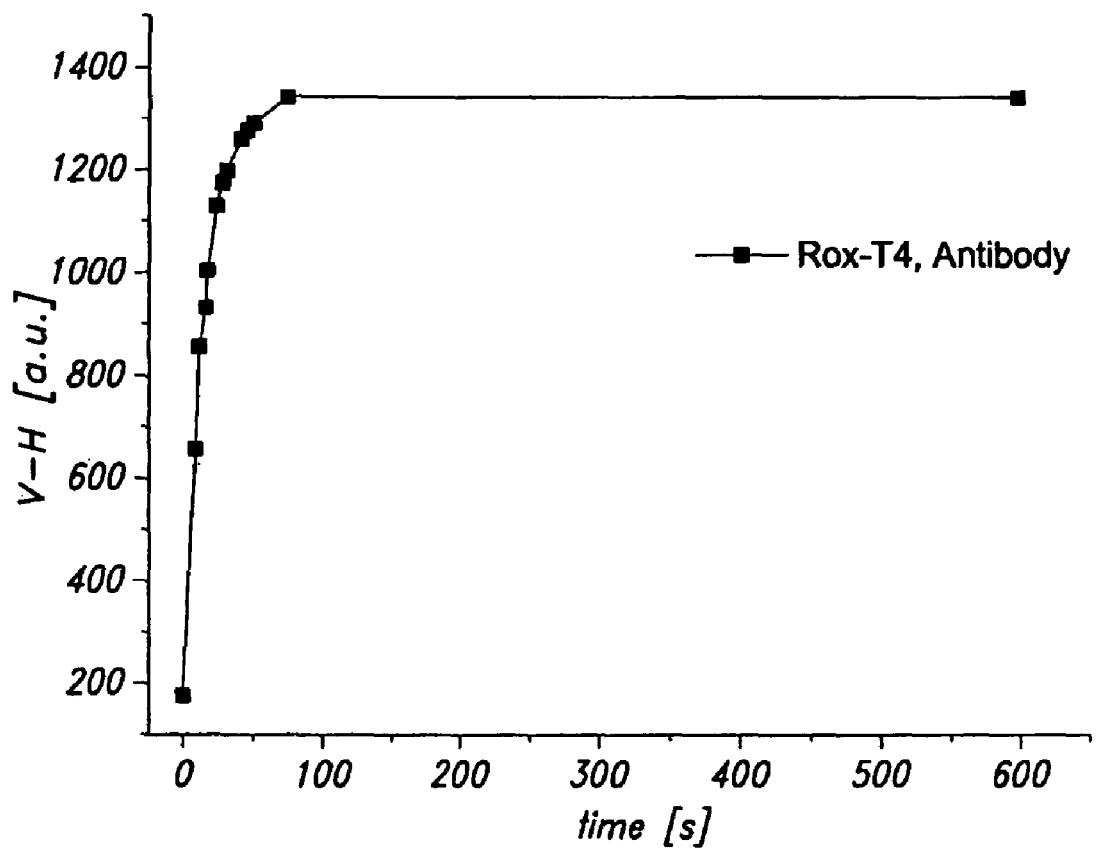
FIG. 3 is a graph of a kinetic curve measurable in the presence of a additive using a rhodamine-labeled thyroxine/anti-thyroxine system.

These results are shown graphically in FIG. 3. The results indicate that an increase in the values of P, V–H and V+H occurs over the 600 second time course of the reaction.

Since the reaction between the fluorescent conjugate and its antibody is measurable, a study of the inhibition of the binding of the fluorescent conjugate by a sample thought to contain an analyte of interest is carried out. In particular, a change in the initial rate of polarized fluorescence intensity difference PFID (V–H) is monitored as a function of analyte in the sample.

The amount of analyte in the sample is determined by measuring the binding of the fluorescent conjugate to the specific binding component in the presence of the sample and determining the amount of analyte in the sample from a standard curve. Such a standard curve is constructed by first measuring the binding of the fluorescent conjugate to its specific binding partner (e.g., its specific antibody) and determining the extent of inhibition of this binding by different known quantities of unlabeled analyte. The standard curve is then constructed, which shows the degree of binding by the labeled analyte as a function of the quantity of the unlabeled analyte.

Example 6

Influence of Sodium Benzoate Combined with an Organic Solvent on the Rate of the Reaction Between F-Thyroxine and Anti-Thyroxine and on the Non-Specific Binding of Serum Components The present example shows the influence of sodium benzoate combined with 10% 2-propanol on the velocity of the reaction between fluorescent hapten (F-thyroxine) and anti-thyroxine, and on the initial non-specific binding between F-thyroxine and serum components. The buffer and stock solutions described in Example 1 and the measurement methodology described in Example 2 were used.
Experimental Conditions:
Fluorescein-Thyroxine (1 nM)
Anti-Thyroxine (1:300 dilution)
PBS with 10% 2-propanol
Benzoate in different concentrations
At t=0 s antibody was pipetted into the cuvette.
A 3 ml cuvette was used, the total volume in the cuvette was 2 ml. A small magnetic stirrer was used for mixing In example 6, the reactions between F-Thyroxine and Anti-Thyroxine, which were carried out in the presence of serum under different reaction conditions, are compared (FIG. 4). There are seven different amounts of sodium benzoate, between 0 and 1.0 Molar in the cuvette. The reaction was performed in a phosphate buffered saline buffer containing 10% 2-propanol. The table in FIG. 4 lists the two important parameters. The first column shows the rate of change in polarization value after five seconds (t=5). The second column shows the polarization value before the addition of antibody (t=0).

In reaction 6-1, the buffer background fluorescence was measured and blanked. F-thyroxine was added and mixed.

The polarization value was observed to be 100 mP. Antibody (anti-T4) was added, stirred, and at t=5 s the rate of change of P was observed to be 25 mP/s.

In reaction 6-2, the buffer contained an additional 5 µL serum. The background fluorescence was measured and blanked. F-thyroxine was added and mixed. The polarization value was observed to be 195 mP. Antibody (anti-T4) was added, stirred, and at t=5 s the rate of change of P was observed to be 9.7 mP/s.

The interaction between serum proteins and/or other serum components and F-thyroxine was quite strong, as the difference between the measured mP value before and after addition of serum almost doubled. The reaction rate between F-thyroxine and its antibody was also affected by the presence of serum, as it slowed to less than half its value.

In experiments 6-3 through 6-7, the effect of increasing sodium benzoate, was be observed to perform two tasks. The first was to slow the reaction rate down to about 30% its value from zero additive agent (9.7 to 3.2). The second was the elimination of non-specific binding, as expressed by the decrease of the mP value due to the interaction with serum. This was reduced from 195 down to 100, equivalent to the original mP value before the addition of serum as observed in experiment 6-1.

Example 7

Figure 5:
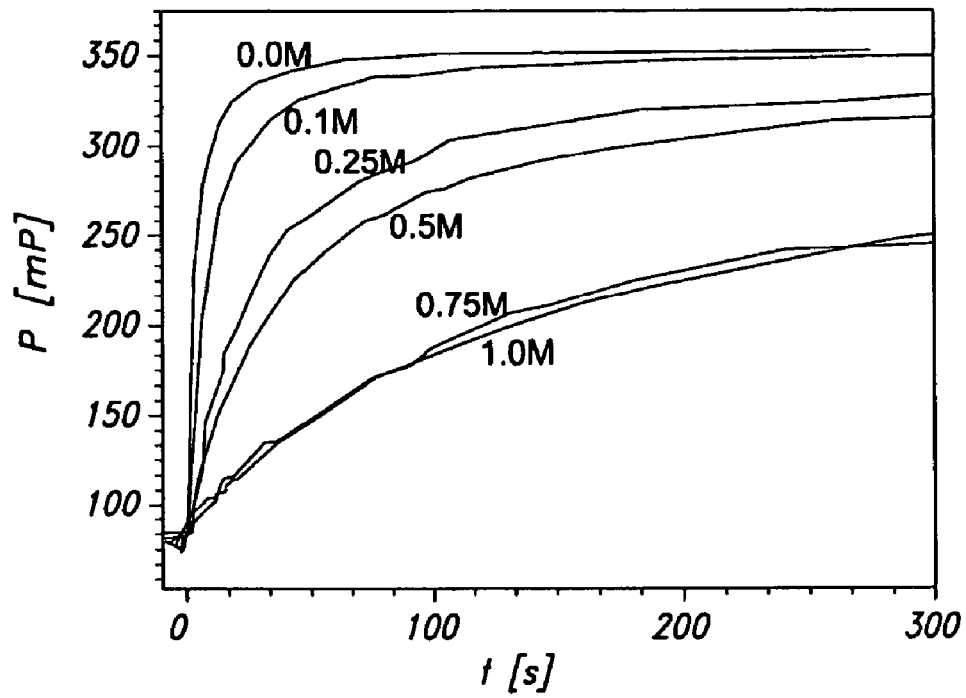
FIG. 5 is a graph of the effects on a fluorescecin-T4/anti-T4 reaction performed in a PBS buffer containing an 5% 2-propanol and differing amounts of sodium benzoate in the absence of non-specific binding substances.

Influence of Sodium Benzoate Combined with an Organic Solvent on the Velocity of the Reaction Between F-Thyroxine and Anti-Thyroxine in the Absence of Non-Specific Binding Components The present example shows the influence of sodium benzoate in the absence of serum or other non-specific binding components, on the antibody reaction velocity between F-thyroxine and anti-T4 when the reaction was performed in a PBS buffer containing an additional 5% 2-propanol (FIG. 5). The buffer and stock solutions described in Example 1 and the measurement methodology described in Example 2 were used.
Experimental Conditions:
Fluorescein-Thyroxine, 1 nM
Anti-Thyroxine (1:300)
PBS with 5% 2-propanol
Sodium Benzoate in different concentrations From this experiment, it was observed that the reaction rate between F-thyroxine and antibody slowed dramatically as the concentration of sodium benzoate increased to 1.0 molar.

Example 8

Figure 6:
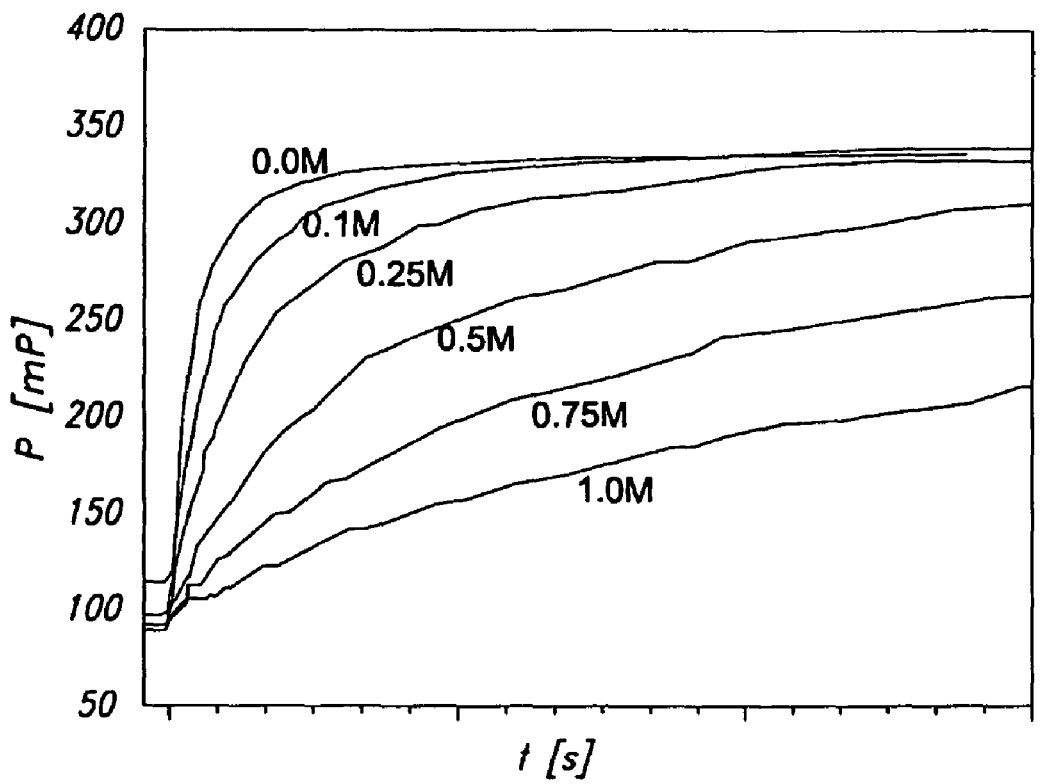
FIG. 6 is a graph of the effects on a fluorescein-T4/anti-T4 system using differing concentrations of sodium benzoate combined with 5% 2-propanol in the presence of the non-specific binding substance BSA.

Influence of Sodium Benzoate Combined with an Organic Solvent on the Velocity of the Reaction Between F-Thyroxine and Anti-Thyroxine and on Non-Specific Binding of BSA The present example shows the influence of sodium benzoate in the presence of the non-specific binding substance BSA, on the antibody reaction velocity between F-thyroxine and anti-T4 and on the non-specific binding between F-thyroxine and BSA (FIG. 6) when the reaction was performed in a PBS buffer containing an additional 5% 2-propanol. The buffer and stock solutions described in Example 1 and the measurement methodology described in Example 2 were used.
Experimental Conditions:
Fluorescein-Thyroxine, 1 nM
Anti-Thyroxine (1:300)
PBS with 5% 2-propanol
BSA 0.1 µM
Sodium benzoate in different concentrations It was observed that the non-specific binding due to the presence of BSA was reduced by the addition of the additive, as seen by the lowering of the initial P value with respect to the measurement without the additive. It was also observed that the rate of the antibody reaction was substantially slowed by the addition increasing concentrations of sodium benzoate.

Example 9

Figure 7:
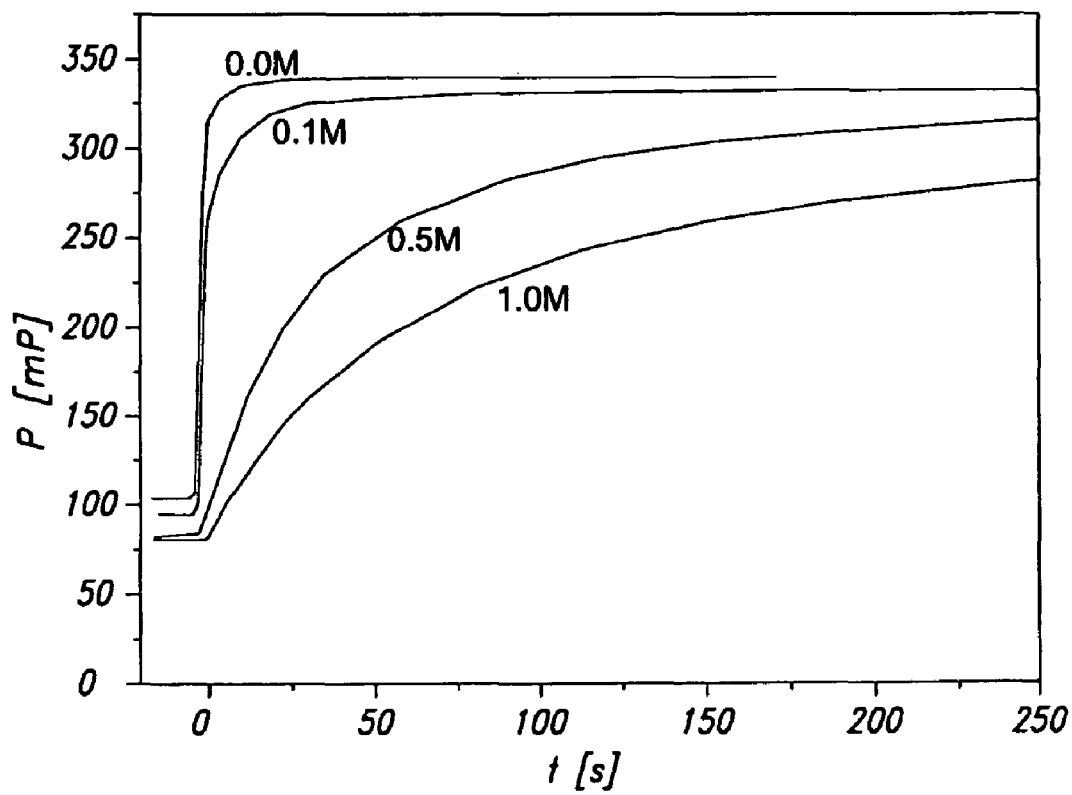
FIG. 7 is a graph of the effects on a fluorescein-T4/anti-T4 system using differing concentrations of guanidine hydrochloride combined with 5% 2-propanol.

Influence of Guanidine Hydrochloride Combined with an Organic Solvent on the Velocity of the Reaction Between F-Thyroxine and Anti-Thyroxine and on Non-Specific Binding of BSA The present example shows the influence of guanidine hydrochloride on the antibody reaction velocity between F-thyroxine and anti-thyroxine in the presence of the non-specific binding substance BSA and on the non-specific binding between F-thyroxine and BSA (FIG. 7) when the reaction was performed in a PBS buffer containing an additional 5% 2-propanol. The buffer and stock solutions described in Example 1 and the measurement methodology described in Example 2 were used.
Experimental Conditions:
Fluorescein-Thyroxine, 1 nM
Anti-Thyroxine (1:300)
PBS with 5% 2-propanol
BSA 0.1 µM
Guanidine hydrochloride in different concentrations It was observed that the non-specific binding due to the presence of BSA was reduced by the addition of the additive, as seen by the lowering of the initial P valve with respect to the measurement without the additive. It was also observed that the rate of the reaction was substantially slowed by the addition of increasing concentrations of guanidine hydrochloride.

Example 10

Figure 8:
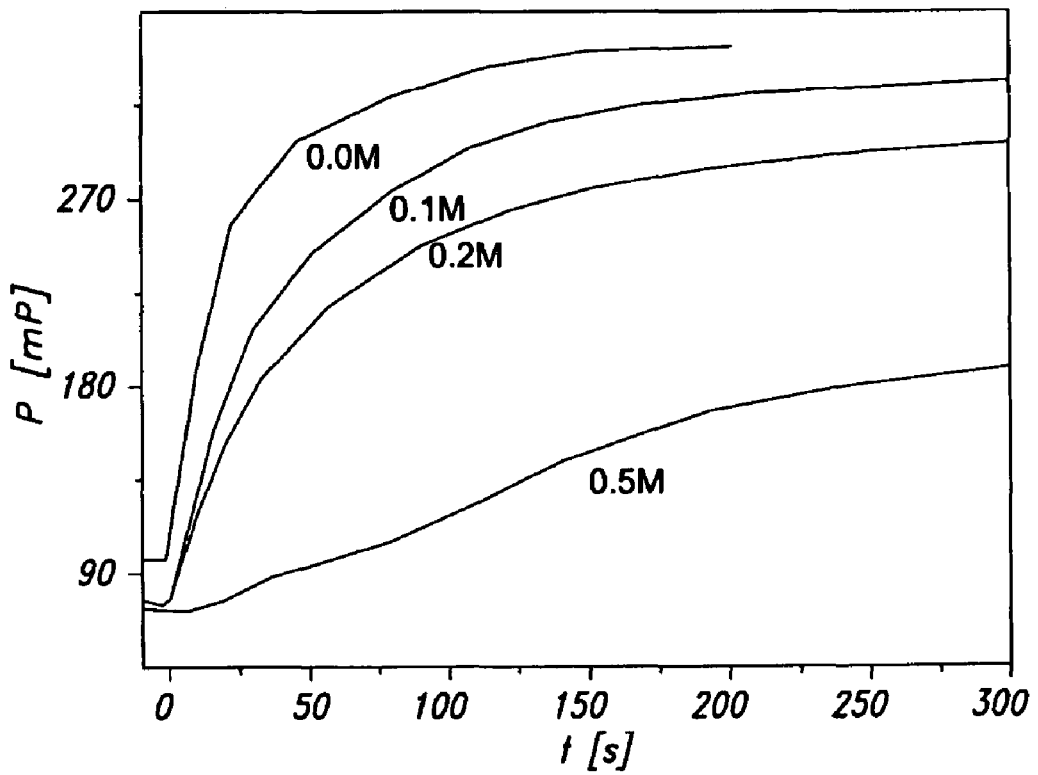
FIG. 8 is a graph of the effects on a fluorescein-T4/anti-T4 system using differing concentrations of sodium dichloroacetate combined with 5% 2-propanol.

Influence of Sodium P-Tolulene Sulfonate Combined with an Organic Solvent on the Velocity of the Reaction Between F-Thyroxine and Anti-Thyroxine and on Non-Specific Binding of BSA The present example shows the influence of sodium p-toluene sulfonate on the antibody reaction velocity between F-thyroxine and anti-thyroxine in the presence of the non-specific binding substance BSA and on the non-specific binding between F-thyroxine and BSA (FIG. 8) when the reaction was performed in a PBS buffer containing an additional 5% 2-propanol. The buffer and stock solutions described in Example 1 and the measurement methodology described in Example 2 were used.
Experimental Conditions:
Fluorescein-Thyroxine, 1 nM
Anti-Thyroxine (1:300)
PBS with 5% 2-propanol
BSA 0.1 µM
Sodium p-toluene sulfonate in different concentrations It was observed that the non-specific binding due to the presence of BSA was reduced by the addition of the additive, as seen by the lowering of the initial P value with respect to the measurement without the additive. It was also observed that the rate of the reaction was substantially slowed by the addition of increasing concentrations of sodium p-tolulene sulfonate.

Example 11

Figure 9:
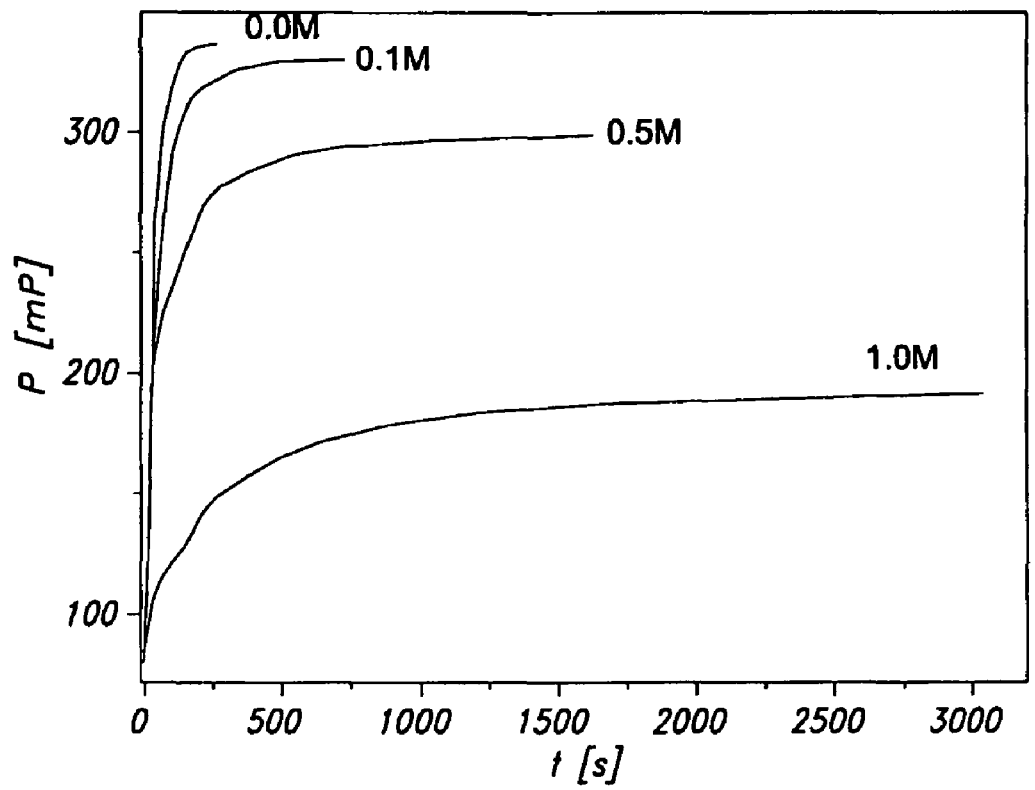
FIG. 9 is a graph of the effects on a fluorescein-T4/anti-T4 system using differing concentrations of potassium benzoate combined with 4.75% 2-propanol.

Influence of Potassium Benzoate Combined with an Organic Solvent on the Velocity of the Reaction Between F-Thyroxine and Anti-Thyroxine and on Non-Specific Binding of BSA The present example shows the influence of potassium benzoate on the antibody reaction velocity between F-thyroxine and anti-thyroxine in the presence of the non-specific binding substance BSA and on the non-specific binding between F-thyroxine and BSA (FIG. 9) when the reaction was performed in a PBS buffer containing an additional 4.75% 2-propanol. The buffer and stock solutions described in Example 1 and the measurement methodology described in Example 2 were used.
Experimental Conditions:
Fluorescein-Thyroxine, 1 nM
Anti-Thyroxine (1:300)
PBS with 4.75% 2-propanol
BSA 0.1 µM
Potassium benzoate in different concentrations It was observed that the non-specific binding due to the presence of the BSA was reduced by the addition of the additive, as seen by the lowering of the initial P value with respect to the measurement without the additive. It was also observed that the rate of the reaction was substantially slowed by the addition of increasing concentrations of potassium benzoate.

Example 12

Figure 10:
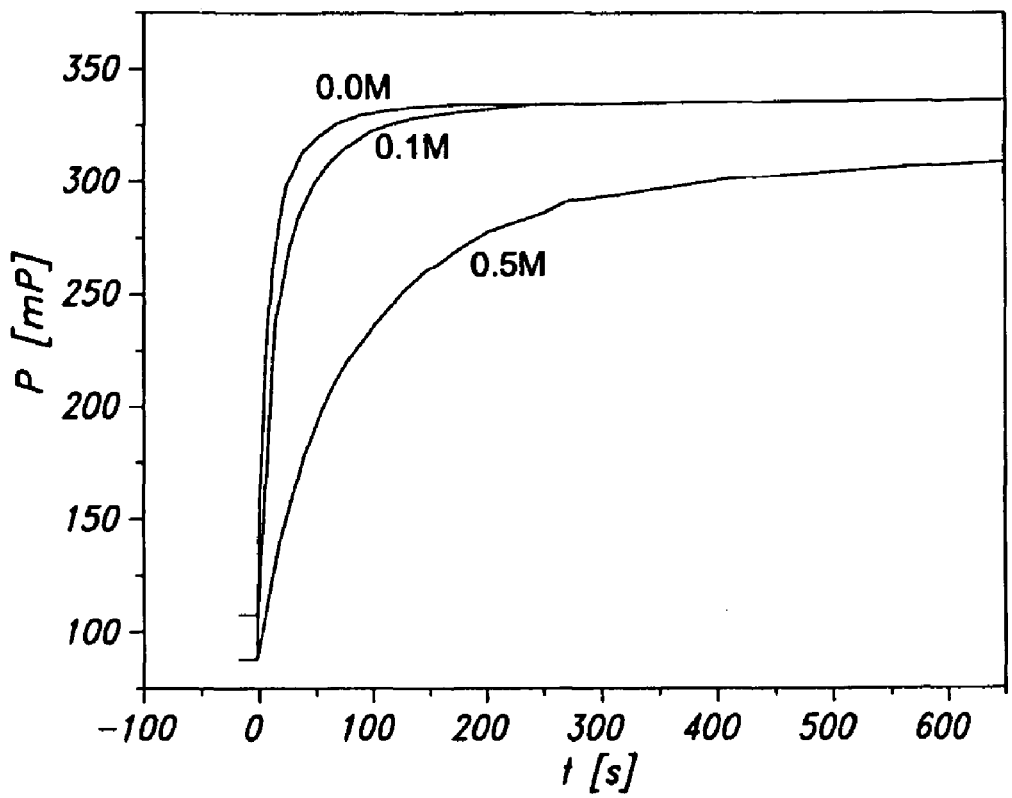
FIG. 10 is a graph of the effects on a fluorescein-T4/anti-T4 system using differing concentrations of sodium chloroacetate combined with 4.75% 2-propanol.

Influence of Sodium Chloroacetate Combined with an Organic Solvent on the Velocity of the Reaction Between F-Thyroxine and Anti-Thyroxine and on Non-Specific Binding of BSA The present example shows the influence of sodium chloroacetate on the antibody reaction velocity between F-thyroxine and anti-thyroxine in the presence of the non-specific binding substance BSA and on the non-specific binding between F-thyroxine and BSA (FIG. 10) when the reaction was performed in a PBS buffer containing an additional 4.75% 2-propanol. The buffer and stock solutions described in Example 1 and the measurement methodology described in Example 2 were used.
Experimental Conditions:
Fluorescein-Thyroxine, 1 nM
Anti-Thyroxine (1:300)
PBS with 4.75% 2-propanol
BSA 0.1 µM
Sodium chloroacetate in different concentrations It was observed that the non-specific binding due to the presence of BSA was reduced by the addition of the additive. It was also observed that the rate of the reaction was substantially slowed by the addition of increasing concentrations of sodium chloroacetate.

Example 13

Figure 11:
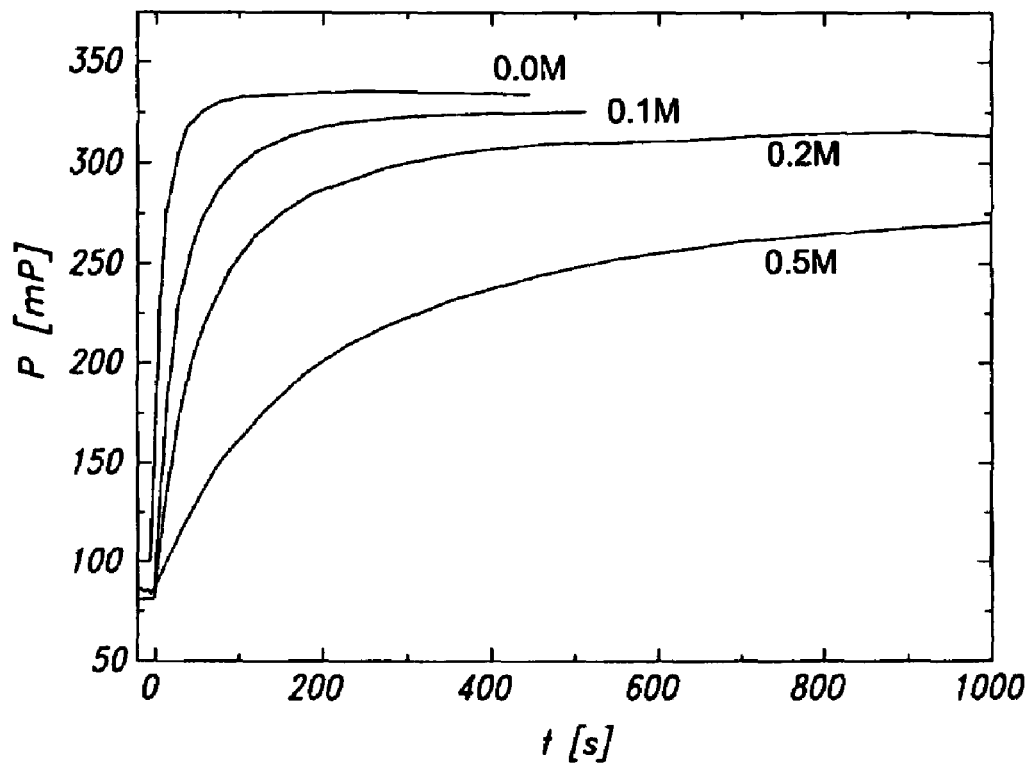
FIG. 11 is a graph of the effects on a fluorescein-T4/anti-T4 system using differing concentrations of sodium dichloroacetate combined with 4.75% 2-propanol.

Influence of Sodium Dichloroacetate Combined with an Organic Solvent on the Velocity of the Reaction Between F-Thyroxine and Anti-Thyroxine and on Non-Specific Binding of BSA The present example shows the influence of sodium dichloroacetate on the antibody reaction velocity between F-thyroxine and anti-thyroxine in the presence of the non-specific binding between F-thyroxine and BSA (FIG. 11) when the reaction was performed in a PBS buffer containing an additional 4.75% 2-propanol. The buffer and stock solutions described in Example 1 and the measurement methodology described in Example 2 were used.
Experimental Conditions:
Fluorescein-Thyroxine, 1 nM
Anti-Thyroxine (1:300)
PBS with 4.75% 2-propanol
BSA 0.1 µM
Sodium dichloroacetate in different concentrations It was observed that the non-specific binding due to the presence of BSA was reduced by the addition of the additive, as seen by the lowering of the initial P valve with respect to the measurement without the additive. It was also observed that the rate of the reaction was substantially slowed by the addition of increasing concentrations of sodium dichloroacetate.

Example 14

Figure 12:
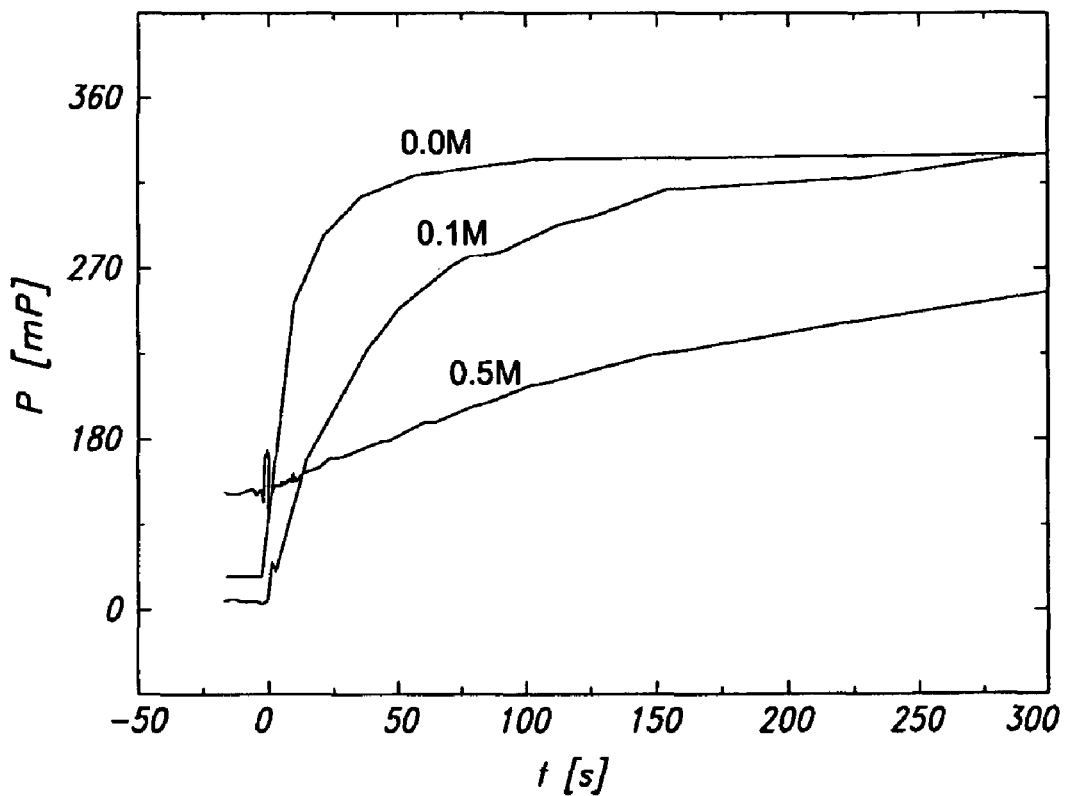
FIG. 12 is a graph of the effects on a fluorescein-T4/anti-T4 system using differing concentrations of sodium salicylate combined with 4.75% 2-propanol.

Influence of Sodium Salicylate Combined with an Organic Solvent on the Velocity of the Reaction Between F-Thyroxine and Anti-Thyroxine and on Non-Specific Binding of BSA The present example shows the influence of sodium salicylate on the antibody reaction velocity between F-thyroxine and anti-thyroxine in the presence of the non-specific binding substance BSA and on the non-specific binding between F-thyroxine and BSA (FIG. 12) when the reaction was performed in a PBS buffer containing an additional 4.75% 2-propanol. The buffer and stock solutions described in Example 1 and the measurement methodology described in Example 2 were used.
Experimental Conditions:
Fluorescein-Thyroxine, 1.5 nM
Anti-Thyroxine (1:300)
PBS with 4.75% 2-propanol
BSA 0.1 µM
Sodium Salicylate in different concentrations It was observed that the non-specific binding due to the presence of BSA was reduced by the addition of the additive, as seen by the lowering of the initial P valve with respect to the measurement without the additive. It was also observed that the rate of the reaction was substantially slowed by the addition of increasing concentrations of sodium salicylate.

Example 15

Figure 13:
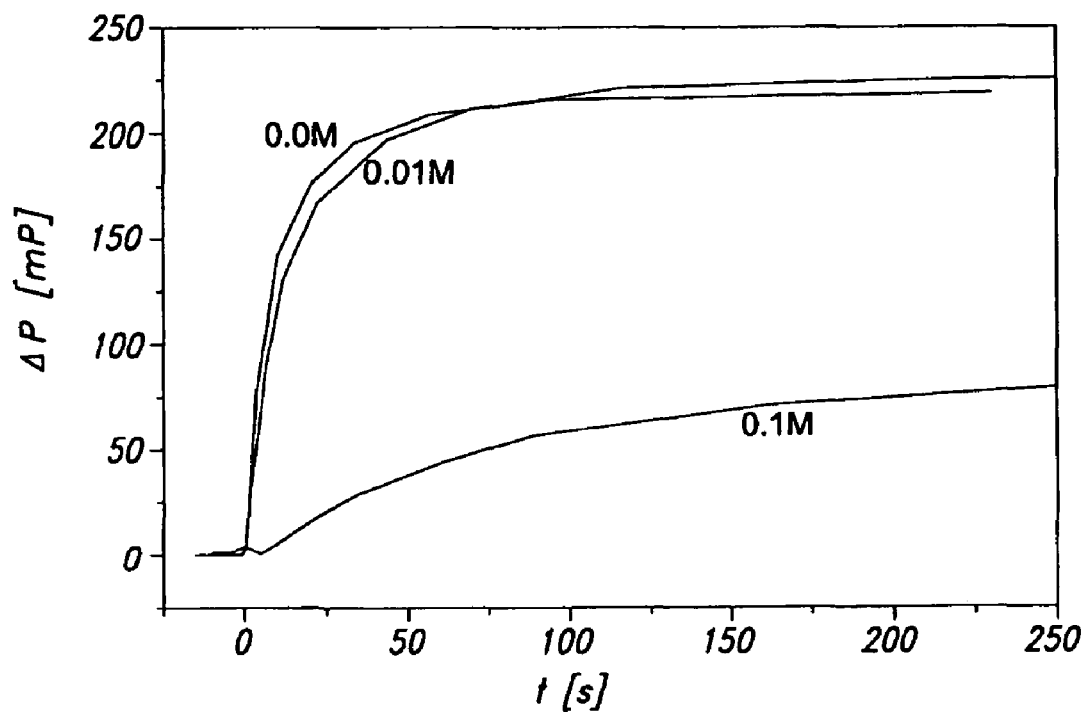
FIG. 13 is a graph of the effects on a fluorescein-T4/anti-T4 system using differing concentrations of N-hydroxysuccinimide combined with 4.75% 2-propanol.

Influence of N-Hydroxysuccinimide Combined with an Organic Solvent on the Velocity of the Reaction Between F-Thyroxine and Anti-Thyroxine and on Non-Specific Binding of BSA The present example shows the influence of N-hydroxysuccinimide on the antibody reaction velocity between F-thyroxine and anti-thyroxine in the presence of the non-specific binding substance BSA and on the non-binding specific binding between F-thyroxine and BSA (FIG. 13) when the reaction was performed in a PBS buffer containing an additional 4.75% 2-propanol and non-specific binding of fluorophore and BSA (FIG. 13). The buffer and stock solutions described in Example 1 and the measurement methodology described in Example 2 were used.

Experimental Conditions:
Fluorescein-Thyroxine, 1.5 nM
Anti-Thyroxine (1:300)
PBS with 4.75% 2-propanol
BSA 0.1 µM
N-Hydroxysuccinimide in different concentrations The ΔP diagram shows the difference of the P value of the free fluorescence labelled compound and its P value during the reaction, where $\Delta P = P - P_{t=0}$. This shows the increase of the P value due only to the binding of analyte and antibody. It was observed that the non-specific binding due to the presence of BSA was slightly reduced by the addition of the additive. It was also observed that the rate of the reaction was substantially slowed by the addition of increasing concentrations of N-hydroxysuccinimide.

Example 16

Figure 14:
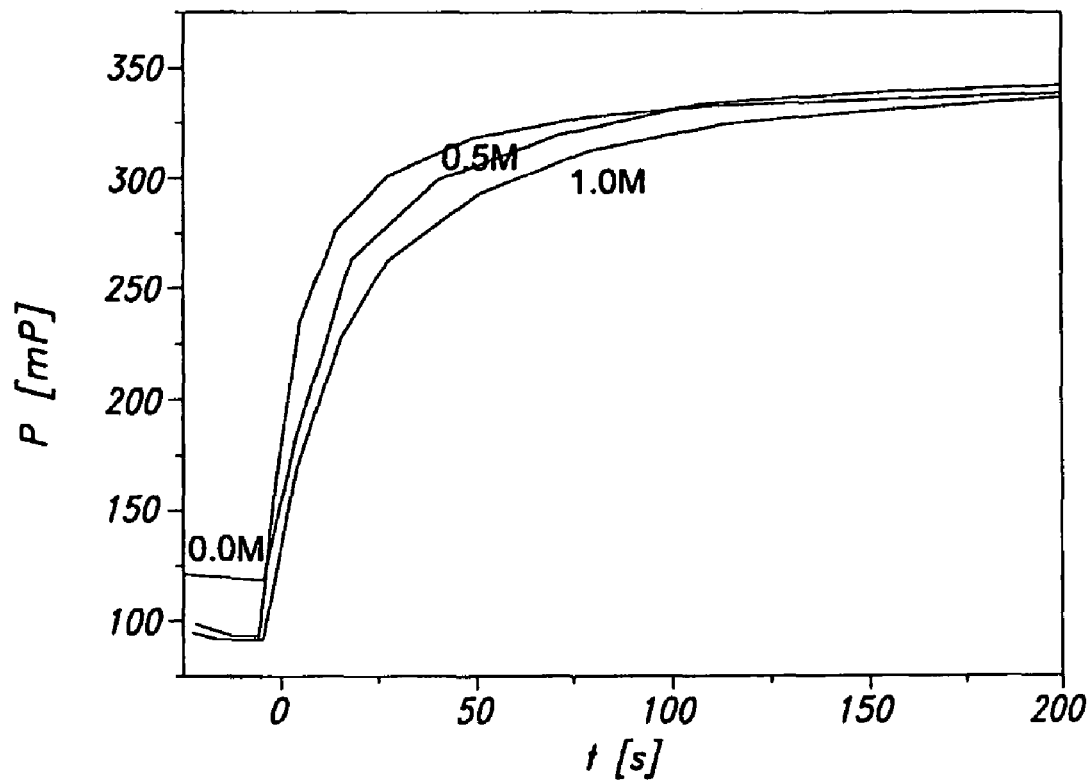
FIG. 14 is a graph of the effects on a fluorescein-T4/anti-T4 system using differing concentrations of sodium chloride combined with 4.75% 2-propanol.

Influence of Sodium Chloride Combined with an Organic Solvent on the Velocity of the Reaction Between F-Thyroxine and Anti-Thyroxine and on Non-Specific Binding of BSA The present example shows the influence of sodium chloride on the antibody reaction velocity between F-thyroxine and anti-thyroxine in the presence of the non-specific binding substance BSA and on the non-specific binding between F-thyroxine and BSA (FIG. 14) when the reaction was performed in a PBS buffer containing an additional 4.75% 2-propanol. The buffer and stock solutions described in Example 1 and the measurement methodology described in Example 2 were used.

Experimental Conditions:
Fluorescein-Thyroxine, 1.5 nM
Anti-Thyroxine (1:300)
PBS with 4.75% 2-propanol
BSA 0.1 µM
Sodium Chloride in different concentrations It was observed that the non-specific binding due to the presence of BSA was reduced by the addition of the additive. However, it was also observed that the rate of the reaction was not substantially slowed by the addition of increasing concentrations of sodium chloride thereby making the antibody reaction more difficult to study in the presence of sodium chloride relative to in the presence of other salt agents.

Example 17

Figure 15:
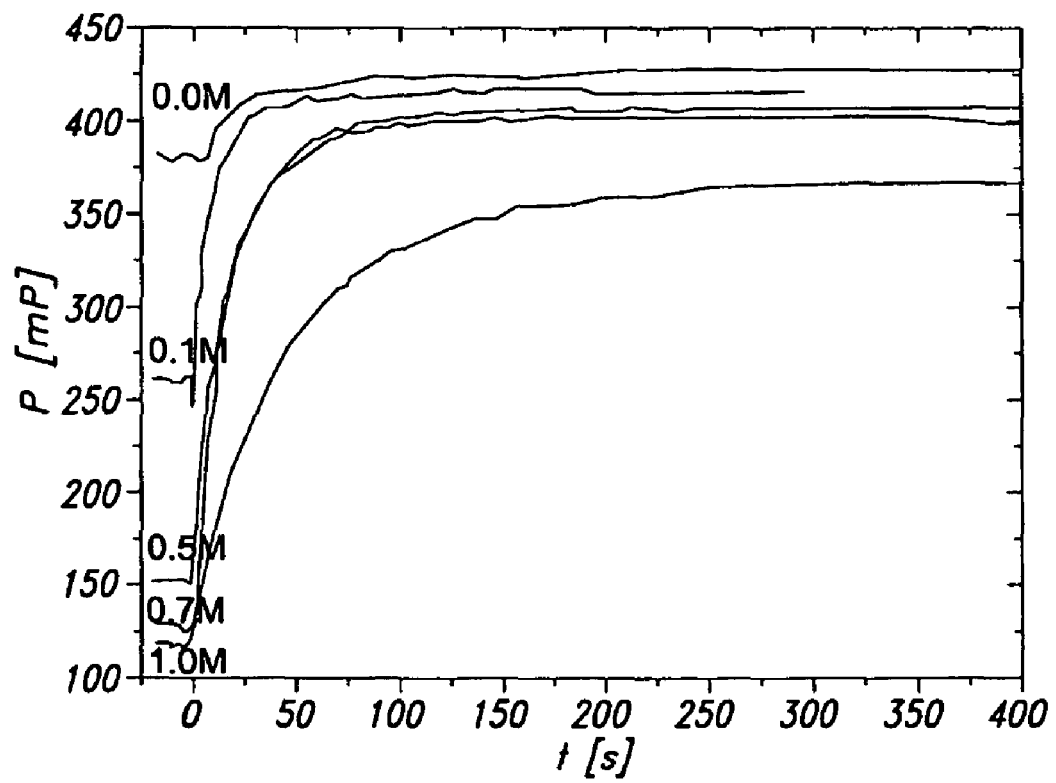
FIG. 15 is a graph of the effects on a rhodamine-T4/anti-T4 system using differing concentrations of sodium benzoate combined with 10% 2-propanol.

Effects of Sodium Benzoate Combined with an Organic Solvent on the Velocity of the Reaction Between Rhodamine-Thyroxine and Anti-Thyroxine and on Non-Specific Binding of Serum Components The present example shows the effects in a Rhodamine-Thyroxine/Anti Thyroxine system of different amounts of sodium benzoate in serum and at a higher concentration of alcohol (FIG. 15). The serum was diluted 1:500 in PBS/10% 2-propanol. The buffer and stock solutions, as well as the measurement methodology described in Example 5 were used.

Experimental Conditions:
Rox-Thyroxine, 1.5 nM
Anti-Thyroxine (1:300)
PBS with 10% 2-propanol
Serum 1:500
Sodium benzoate in different concentrations It was observed that the non-specific binding due to the presence of serum components was substantially reduced by the addition of this combination of additives. It was also observed that the rate of the reaction was substantially slowed by the addition of increasing concentrations of sodium benzoate.

Example 18

Figure 16:
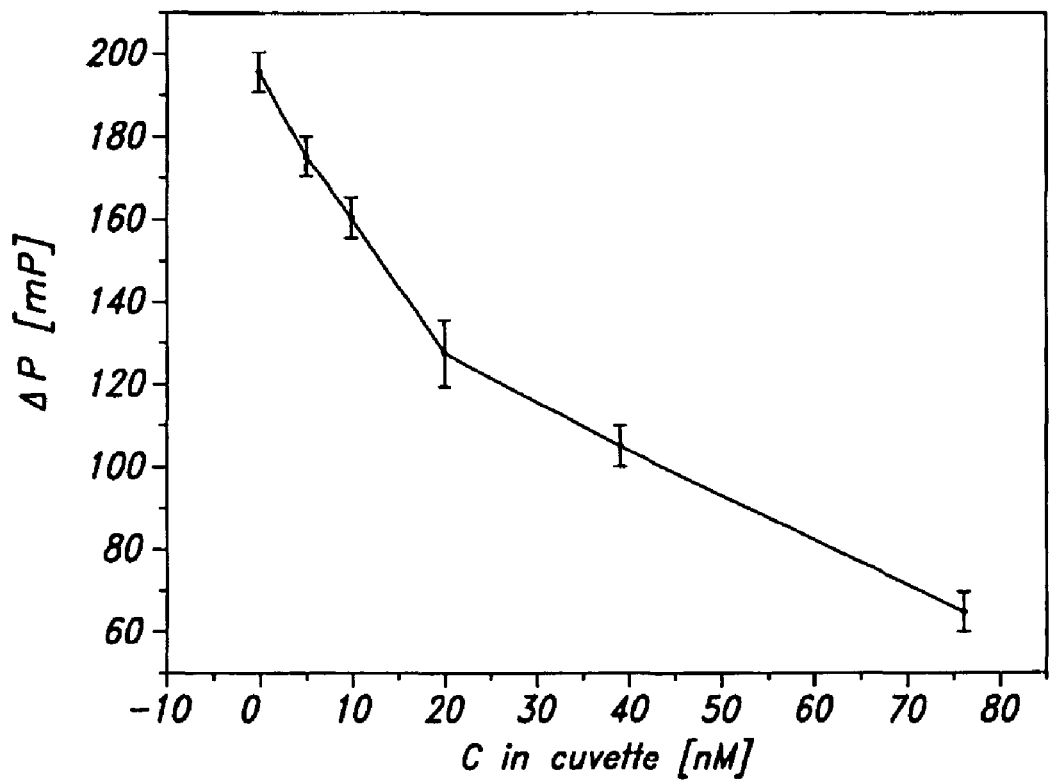
FIG. 16 is a graph of a Standard Calibration Curve of a rhodamine-T4/anti-T4 in the presence of sodium benzoate combined with 10% 2-propanol in the presence of serum.

Standard Curve Constructed by Monitoring for a Change in the Initial Rate of Polarization as a Function of Different Known Quantities of the Analyte Thyroxine The present example is directed to an experiment, such as in Example 17, performed in serum, and shows that the antibody reaction between Rox-thyroxine and anti-thyroxine can be performed in the presence of additive (FIG. 16). In particular, FIG. 16 shows a calibration curve, measured in the following conditions:
1500 µl Serum diluted 1:500 with (PBS buffer containing 10% 2-propanol and 0.7 M sodium benzoate)
1.5 nM Rox-Thyroxine and 20 µl anti-Thyroxine (1:300 dilution)

The x-axis of the graph in FIG. 16 is the concentration (nM) of analyte thyroxine in the cuvette. From the standard curve, it is possible to measure unknown quantities of the analyte.

What is claimed is:

1. A method of lowering the rate of a reaction in an assay for the detection and/or measurement of an analyte in a sample, comprising:
    (a) providing a reaction mixture comprising at least two components selected from the group consisting of (i) a fluorescent conjugate of the analyte; (ii) a component capable of specifically binding to the analyte and its fluorescent conjugate; and (iii) a sample, which comprises or is suspected to comprise the analyte;
    (b) providing the component not selected in step (a):
    (c) allowing the selected components in the reaction mixture to interact;
    (d) adding non-physiological amounts of at least one additive to the reaction mixture or the component of step (b) or both;
    (e) combining the reaction mixture and the step (b) component; and
    (f) monitoring for the rate of change of the concentration of a complex formed due to the combination of the components in step (a) and (b) to determine the concentration of the analyte in the sample.

2. The method of claim 1, wherein the additive decreases the rate of the reaction from about $10^6 M^{-1} sec^{-1}$ or greater to about $10^5 M^{-1} sec^{-1}$ or less.

3. The method of claim 1, wherein an association rate constant for a specific binding reaction of the fluorescent conjugate with the specific binding component decreases upon the addition of the non-physiological amounts of the additive.

4. The method of claim 1, wherein the additive is present in an amount of about 0.5 M to about 1.5 M or higher in the reaction mixture.

5. The method of claim 1, wherein the additive is present in an amount of about 5% to about 20% (weight/volume) of the reaction mixture.

6. The method of claim 1, wherein the additive is a salt of an anion selected from the group consisting of salicylate, trichloroacetate, thiocyanate, perchlorate and benzoate.

7. The method of claim 1, wherein the additive is selected from the group consisting of 8-anilino-1-napthalene-sulfonic acid, 2-Guanidinobenzimidazole, 2,3,5-triacetylguanosine, Benzimidazolylurea, acetamide, 2,2'-azino-bis(3-ethylbenzthiazoline-6-sulfonic acid), sodium trichloroacetate, sodium deoxycholate, creatine benzimidazole, sodium p-toluene-sulfonate, sodium dichloro acetate, sodium iodide, sodium fluoride, sodium chloroacetate, 5-benzimidazolecarboxylic acid, Salicylamide, guanidine hydrochloride, sodium chloride, 2-benzimidazole-proprionic acid, 2-benzimidazolemethanol, Sodium chlorodifluoroacetate, 4-guanidinobenzoic acid, 3-chlorobenzoic acid, N-hydroxy succinimide, guanidine and Potassium benzoate, organic solvents and combinations thereof.

8. The method of claim 1, wherein the additive affects the order of reaction with respect to the fluorescent conjugate and the specific binding component.

9. The method of claim 1, wherein the additive is present in a sufficient amount to make the binding reaction first order with respect to the concentration of each of the fluorescent conjugate and the specific binding component.

10. The method of claim 1, wherein the assay is a fluorescence polarization assay.

11. The method of claim 1, wherein the monitoring step comprises monitoring for a change in the initial rate of polarization as a function of an amount of analyte in the sample.

12. The method of claim 1, wherein the monitoring step comprises measuring the binding of the fluorescent conjugate to the specific binding component; and determining the extent of inhibition of this binding by different known quantities of unlabeled analyte.

13. The method of claim 11, wherein the monitoring step further comprises constructing a standard curve which shows the degree of binding by the fluorescent conjugate as a function of the quantity of the unlabeled analyte.

14. The method of claim 12, wherein the monitoring step further comprises determining the amount of analyte in the sample by measuring the binding of the fluorescent conjugate to the specific binding component in the presence of the sample and determining the amount of analyte in the sample from the standard curve.

15. The method of claim 1, wherein the analyte is an organic contaminant.

16. The method of claim 1, wherein the organic contaminant is of environmental concern.

17. The method of claim 15, wherein the organic contaminant is a fungal or microbial toxin.

18. The method of claim 1, wherein the analyte is a drug.

19. The method of claim 1, wherein the analyte is a steroid or hormone.

20. The method of claim 1, wherein the analyte is a protein or peptide.

21. The method of claim 1, wherein the analyte is a lipid or sugar.

22. The method of claim 1, wherein the specific binding component is an antibody.

23. The method of claim 1, wherein the specific binding component is a receptor.

24. The method of claim 1, wherein the specific binding component is on a solid substrate.

25. The method of claim 24, wherein the solid substrate is selected from the group consisting of glass, plastic and paper.

26. The method of claim 1, wherein the fluorescent conjugate comprises a fluorescent dye.

27. The method of claim 26, wherein the fluorescent dye is selected from the group consisting of fluorescein, rhodamine and derivatives thereof.

28. The method of claim 1, wherein the fluorescent conjugate comprises thyroxine.

29. The method of claim 28, wherein the specific binding component is anti-thyroxine.

30. A method of lowering the rate of a reaction in an assay for the detection and/or measurement of an analyte in a sample, comprising:
(a) providing (i) a fluorescent conjugate of the analyte; (ii) a component capable of specifically binding to the analyte and its fluorescent conjugate; and (iii) a sample, which comprises or is suspected to comprise the analyte;
(b) allowing component (ii) to interact with the fluorescent conjugate of the analyte and the analyte in the sample, thereby forming a detectable complex due to the reaction between the fluorescent conjugate of the analyte and component (ii), wherein the reaction is performed in the presence of non-physiological amounts of at least one additive; and
(c) monitoring for the rate of change of the concentration of the complex formed in (b) to determine the concentration of the analyte in the sample.

31. The method of claim 30, wherein the allowed step comprises allowing component (ii) to interact with the fluorescent conjugate of the analyte, followed by the addition of the sample.

32. The method of claim 30, wherein the allowing step comprises allowing component (ii) to interact with the analyte in the sample, followed by the addition of the fluorescent conjugate of the analyte.

33. The method of claim 30, wherein the allowing step comprises allowing component (ii) to simultaneously interact with the fluorescent conjugate of the analyte and the sample.

34. The method of claim 1, wherein the at least one additive is a combination of a salt agent and an organic solvent.

35. The method of claim 30, wherein the at least one additive is a combination of a salt agent and an organic solvent.

* * * * *